(12) United States Patent
Pauly et al.

(10) Patent No.: US 8,735,690 B2
(45) Date of Patent: May 27, 2014

(54) MAIZE VARIETY AND METHOD OF PRODUCTION

(75) Inventors: Markus Pauly, Berkeley, CA (US); Sarah Hake, Bolinas, CA (US); Florian J. Kraemer, Berkeley, CA (US)

(73) Assignees: The Regents of the University of California, Oakland, CA (US); The United States of America, as represented by the Secretary of Agriculture, Washington, DC (US)

( * ) Notice: Subject to any disclaimer, the term of this patent is extended or adjusted under 35 U.S.C. 154(b) by 404 days.

(21) Appl. No.: 13/152,219

(22) Filed: Jun. 2, 2011

(65) Prior Publication Data

US 2011/0302669 A1    Dec. 8, 2011

Related U.S. Application Data

(60) Provisional application No. 61/351,729, filed on Jun. 4, 2010.

(51) Int. Cl.
| | | |
|---|---|---|
| A01H 5/00 | (2006.01) | |
| A01H 1/02 | (2006.01) | |
| A01H 4/00 | (2006.01) | |
| A23K 3/03 | (2006.01) | |

(52) U.S. Cl.
USPC .......... 800/320.1; 426/630; 426/61; 435/412; 800/263; 800/275

(58) Field of Classification Search
None
See application file for complete search history.

(56) References Cited

U.S. PATENT DOCUMENTS

| | | | |
|---|---|---|---|
| 3,710,511 A | 1/1973 | Patterson | |
| 3,861,709 A | 1/1975 | Mulcahy et al. | |
| 4,341,713 A * | 7/1982 | Stolp et al. | 554/17 |
| 4,654,465 A | 3/1987 | Brar et al. | |
| 4,727,219 A | 2/1988 | Brar et al. | |
| 4,936,904 A | 6/1990 | Carlson | |
| 5,432,068 A | 7/1995 | Albertsen et al. | |
| 5,639,951 A | 6/1997 | Bosemark et al. | |
| 7,579,443 B2 * | 8/2009 | Dhugga et al. | 530/372 |
| 2002/0062506 A1 | 5/2002 | Lubich | |
| 2003/0005479 A1 | 1/2003 | Kato | |
| 2003/0221220 A1 * | 11/2003 | Broglie et al. | 800/284 |

FOREIGN PATENT DOCUMENTS

| | | |
|---|---|---|
| EP | 0160390 A2 | 11/1985 |
| EP | 0329308 A2 | 8/1989 |
| WO | 90/08828 A2 | 8/1990 |

OTHER PUBLICATIONS

Boppenmaier et al., "Comparisons among Strains of Inbreds for RFLPs", Maize Genetics Cooperative Newsletter, vol. 65, 1991, p. 90.

Chalyk et al., "Regular Segregation of Four Recessive Marker Genes among Maternal Haploids in Maize", Plant Breeding, vol. 119, 2000, pp. 363-364.
Chalyk et al., "Transgressive Segregation in the Progeny of a Cross between Two Inducers of Maize Maternal Haploids", MNL, vol. 68, 1994, p. 47.
Chalyk, S. T., "Creating New Haploid-Inducing Lines of Maize", Maize Genetics Cooperative Newsletter, vol. 73, 1999, pp. 53-54.
Chalyk, S. T., "Properties of Maternal Haploid Maize Plants and Potential Application to Maize Breeding", Euphytica, vol. 79, 1994, pp. 13-18.
Chase, Sherret S., "Production of Homozygous Diploids of Maize from Monoploids", Agronomy Journal, vol. 44, 1952, pp. 263-267.
Coe, Jr, E. H., "A Line of Maize with High Haploid Frequency", The American Naturalist, vol. 93, No. 873, Nov.-Dec. 1959, pp. 381-382.
Coe, Jr. et al., "The Detection of Haploids in Maize", The Journal of Heredity, vol. 55, 1964, pp. 231-233.
Colbert et al., "High-Throughput Screening for Induced Point Mutations", Plant Physiology, vol. 126, Jun. 2001, pp. 480-484.
Conger et al., "Somatic Embryogenesis from Cultured Leaf Segments of *Zea mays*", Plant Cell Reports, vol. 6, 1987, pp. 345-347.
Duncan et al., "The Production of Callus Capable of Plant Regeneration from Immature Embryos of Numerous *Zea mays* Genotypes", Planta, vol. 165, 1985, pp. 322-332.
Foster et al., "Comprehensive Compositional Analysis of Plant Cell Walls (Lignocellulosic biomass) Part II: Carbohydrates", Journal of Visualized Experiments, vol. 32, 2010, 4 pages.
Greenblatt et al., "A Commercially Desirable Procedure for Detection of Monoploids in Maize", The Journal of Heredity, vol. 58, 1967, pp. 9-13.
Heaton et al., "Meeting US Biofuel Goals with Less Land: the Potential of Miscanthus", Global Change Biology, vol. 14, 2008, pp. 2000-2014.
Hoffman, George R., "Genetic Effects of Dimethyl Sulfate, Diethyl Sulfate, and Related Compounds", Mutation Research, vol. 75, 1980, pp. 63-129.
Kato, A., "Single Fertilization in Maize", The Journal of Heredity, vol. 90, No. 2, 1999, pp. 276-280.
Kato, Akio, "Heterofertilization Exhibited by Using Highly Haploid Inducing Line "stock 6" and Supplementary Cross", Maize Genet. Coop. Newsletter, vol. 65, 1990, pp. 109-110.
Kato, Akio, "Induced Single Fertilization in Maize", Sex Plant Reprod., vol. 10, 1997, pp. 96-100.
Kermicle, J. L., "Androgenesis Conditioned by a Mutation in Maize", Science, vol. 166, 1969, pp. 1422-1424.
Knox et al., "Dicamba and Growth Condition Effects on Doubled Haploid Production in Durum Wheat Crossed with Maize", Plant Breeding, vol. 119, 2000, pp. 289-298.
Kobayashi et al., "Haploid Induction and its Genetic Mechanism in Alloplasmic Common Wheat", The Journal of Heredity, vol. 71, 1980, pp. 9-14.

(Continued)

*Primary Examiner* — Cathy Kingdon Worley
*Assistant Examiner* — Jeffrey Bolland
(74) *Attorney, Agent, or Firm* — Morrison & Foerster LLP

(57) ABSTRACT

The disclosure relates to a maize plant, seed, variety, and hybrid. More specifically, the disclosure relates to a maize plant containing a Cal-1 allele, whose expression results in increased cell wall-derived glucan content in the maize plant. The disclosure also relates to crossing inbreds, varieties, and hybrids containing the Cal-1 allele to produce novel types and varieties of maize plants.

18 Claims, 8 Drawing Sheets
(8 of 8 Drawing Sheet(s) Filed in Color)

(56) References Cited

OTHER PUBLICATIONS

Lashermes et al., "Genetic Control of Maternal Haploidy in Maize (*Zea mays* L.) and Selection of Haploid Inducing Lines", Theor Appl. Genet, vol. 76, 1988, pp. 405-410.

Lashermes et al., "Gynogenetic Haploid Plants Analysis for Agronomic and Enzymatic Markers in Maize (*Zea mays* L.)", Theor Appl. Genet, vol. 76, 1988, pp. 570-572.

Li et al., "A Fast Neutron Deletion Mutagenesis-Based Reverse Genetics System for Plants", The Plant Journal, vol. 27, No. 3, 2001, pp. 235-242.

McCallum et al., "Targeted Screening for Induced Mutations", Nature Biotechnology, vol. 18, Apr. 2000, pp. 455-457.

Mehta et al., "Somaclonal Variation for Disease Resistance in Wheat and Production of Dihaploids through Wheat X Maize Hybrids", Genetics and Molecular Biology, vol. 23, No. 3, 2000, pp. 617-622.

Nanda et al., "An Embryo Marker for Detecting Monoploids of Maize (*Zea mays* L.)", Crop Sci., vol. 6, 1965, pp. 213-215.

Pejic et al., "Comparative Analysis of Genetic Similarity among Maize Inbred Lines Detected by RFLPs, RAPDs, SSRs, and AFLPs", Theor Appl. Genet, vol. 97, 1998, pp. 1248-1255.

Pollacsek, M., "Management of the ig Gene for Haploid Induction in Maize", Agronomie, vol. 12, 1991, pp. 247-251.

Rao et al., "Somatic Embryogenesis in Glume Callus Cultures", Maize Genetics Cooperation Newsletter, vol. 60, 1986, pp. 64-65.

Sarkar et al., "A Genetic Analysis of the Origin of Maternal Haploids in Maize", Genetics, vol. 54, Aug. 1966, pp. 453-464.

Sarkar et al., "Origin of Parthenogenetic Diploids in Maize and Its Implications for the Production of Homozygous Lines", Crop Science, vol. 11, Jul.-Aug. 1971, pp. 543-544.

Smith et al., "An Evaluation of the Utility of SSR Loci as Molecular Markers in Maize (*Zea mays* L.): Comparisons with Data from RFLPS and Pedigree", Theor Appl. Genet., vol. 95, 1997, pp. 163-173.

Songstad et al., "Effect of L-Aminocyclopropane-L-Carboxylic Acid, Silver Nitrate, and Norbornadiene on Plant Regeneration from Maize Callus Cultures", Plant Cell Reports, vol. 7, 1988, pp. 262-265.

Verdoodt et al., "Use of the Multi-Allelic Self-Incompatibility Gene in Apple to Assess Homozygocity in Shoots Obtained through Haploid Induction", Theor Appl. Genet, vol. 96, 1998, pp. 294-300.

Wan et al., "Efficient Production of Doubled Haploid Plants through Colchicine Treatment of Anther-Derived Maize Callus", Theor Appl. Genet, vol. 77, 1989, pp. 889-892.

C. Morfin et al. (2007). "Genotyping and confirmation of the Candy Leaf (CAL) gene mutation after introgressions with other breeds of corn," College of Natural Resources, University of California, Berkeley, located at <https://cnr.berkeley.edu/cnrelp/Cesar_M._files/Moorfin-C.pdf>, last visited on Jul. 27, 2011, 1 page.

* cited by examiner

FIG. 7

FIG. 8

SEQUENCE LISTING

```
<160> NUMBER OF SEQ ID NOS: 11

<210> SEQ ID NO 1
<211> LENGTH: 1011
<212> TYPE: DNA
<213> ORGANISM: Zea mays

<400> SEQUENCE: 1
atggcaagca ggcaaggtgt agccgcctcc atgttcgcca cggcattgct cctcggcgtc      60
tttgcatcca tcccacaaag tgctgaggcc atcggggtgt gctacggcat gagcgccaac     120
aacctgccgg cggcgagcac ggtggtgagc atgtacaagg cgaacggcat ctcggcgatg     180
cggctgtacg cgccggacca gggcgcgctg caggcggtgg gcggcacggg catcagcgtg     240
gccgtgggcg cccccaacga cgtgctgtcc aacatcgcgg ctagccccgc ggcggccgcg     300
tcgtgggtgc gcaacaacat ccaggcgtac ccgtccgtgt cgttccgcta cgtgtgcgtg     360
ggcaacgagg tggccggcgg cgcggcgcag gacctggcgc cggccatgga gaacgtgcac     420
gcggcgctgg cggcggccgg gctgggccac atcaaggtga cgacgtcggt gtcgcaggcc     480
atcctgggcg tgtacagccc gccgtccgcc gcggagttca ccggcgaggc gcgcggatac     540
atgggccccg tgctgcagtt cctggcgcgc accgggtcgc cgctcatggc caacatctac     600
ccgtacctgg cctgggcata caacccccagc gccatggaca tgagctacgc gctcttcacc     660
tcctccggca ccgtcgtgca ggacgcgcc tacgggtacc agaacctctt cgacaccacc      720
gtcgacgcct tctacgtcgc catgggcaac aacggcggct ccggcgtgcc gctcgtggtg     780
tcgaagagcg ggtggccgtc cggcgcggc gtccaggcca cgccggccaa cgcgagggtg      840
tacaaccagt acctcatcaa ccacgtcggg cgcgggacgc cgcgccaccc gggcgccatc     900
gagacctacc tcttctccat gttcaacgag aaccagaagg agacggcgt ggagcagaac      960 tggggctct tctaccccaa catgcagcac gtctacccca tcagcttctg a              1011

<210> SEQ ID NO 2
<211> LENGTH: 336
<212> TYPE: PRT
<213> ORGANISM: Zea mays

<400> SEQUENCE: 2

Met Ala Ser Arg Gln Gly Val Ala Ala Ser Met Phe Ala Thr Ala Leu
 1               5                  10                  15
```

```
Leu Leu Gly Val Phe Ala Ser Ile Pro Gln Ser Ala Glu Ala Ile Gly
         20                  25                  30
Val Cys Tyr Gly Met Ser Ala Asn Asn Leu Pro Ala Ala Ser Thr Val
         35                  40                  45
Val Ser Met Tyr Lys Ala Asn Gly Ile Ser Ala Met Arg Leu Tyr Ala
 50                  55                  60
Pro Asp Gln Gly Ala Leu Gln Ala Val Gly Gly Thr Gly Ile Ser Val
 65                  70                  75                  80
Ala Val Gly Ala Pro Asn Asp Val Leu Ser Asn Ile Ala Ala Ser Pro
                 85                  90                  95
Ala Ala Ala Ala Ser Trp Val Arg Asn Ile Gln Ala Tyr Pro Ser
         100                 105                 110
Val Ser Phe Arg Tyr Val Cys Val Gly Asn Glu Val Ala Gly Gly Ala
         115                 120                 125
Ala Gln Asp Leu Ala Pro Ala Met Glu Asn Val His Ala Ala Leu Ala
         130                 135                 140
Ala Ala Gly Leu Gly His Ile Lys Val Thr Thr Ser Val Ser Gln Ala
145                 150                 155                 160
Ile Leu Gly Val Tyr Ser Pro Pro Ser Ala Ala Glu Phe Thr Gly Glu
                 165                 170                 175
Ala Arg Gly Tyr Met Gly Pro Val Leu Gln Phe Leu Ala Arg Thr Gly
         180                 185                 190
Ser Pro Leu Met Ala Asn Ile Tyr Pro Tyr Leu Ala Trp Ala Tyr Asn
         195                 200                 205
Pro Ser Ala Met Asp Met Ser Tyr Ala Leu Phe Thr Ser Ser Gly Thr
210                 215                 220
Val Val Gln Asp Gly Ala Tyr Gly Tyr Gln Asn Leu Phe Asp Thr Thr
225                 230                 235                 240
Val Asp Ala Phe Tyr Val Ala Met Gly Asn Asn Gly Ser Gly Val
                 245                 250                 255
Pro Leu Val Val Ser Lys Ser Gly Trp Pro Ser Gly Gly Val Gln
                 260                 265                 270
Ala Thr Pro Ala Asn Ala Arg Val Tyr Asn Gln Tyr Leu Ile Asn His
         275                 280                 285
Val Gly Arg Gly Thr Pro Arg His Pro Gly Ala Ile Glu Thr Tyr Leu
         290                 295                 300
Phe Ser Met Phe Asn Glu Asn Gln Lys Glu Ser Gly Val Glu Gln Asn
305                 310                 315                 320
Trp Gly Leu Phe Tyr Pro Asn Met Gln His Val Tyr Pro Ile Ser Phe
                 325                 330                 335

<210> SEQ ID NO 3
<211> LENGTH: 1011
<212> TYPE: DNA
<213> ORGANISM: Zea mays

<400> SEQUENCE: 3
atggcaagca ggcaaggtgt agccgcctcc atgttcgcca cggcattgct cctcggcgtc    60
tttgcatcca tcccacaaag tgctgaggcc atcggggtgt gctacggcat gagcgccaac   120
aacctgccgg cggcgagcac ggtggtgagc atgtacaagg cgaacggcat ctcggcgatg   180
cggctgtacg cgccggacca gggcgcgctg caggcggtgg gcggcacggg catcagcgtg   240
gccgtgggcg cccccaacga cgtgctgtcc aacatcgcgg ctagccccgc ggcggccgcg   300
tcgtgggtgc gcaacaacat ccaggcgtac ccgtccgtgt cgttccgcta cgtgtgcgtg   360
```

```
ggcaacgagg tggccggcgg cgcggcgcag gacctggcgc cggccatgga gaacgtgcac    420
gcggcgctgg cggcggccgg gctgggccac atcaaggtga cgacgtcggt gtcgcaggcc    480
atcctgggcg tgtacagccc gccgtccgcc gcggagttca ccggcgaggc gcgcggatac    540
atgggccccg tgctgcagtt cctggcgcgc accgggtcgc cgctcatggc caacatctac    600
ccgtacctgg cctgggcata acccccagc gccatggaca tgagctacgc gctcttcacc     660
tcctccggca ccgtcgtgca ggacggcgcc tacgggtacc agaacctctt cgacaccacc    720
gtcgacgcct tctacgtcgc catgggcaac aacggcggct ccggcgtgcc gctcgtggtg    780
tcggagagcg ggtggccgtc cggcggcggc gtccaggcca cgccggccaa cgcgagggtg    840
tacaaccagt acctcatcaa ccacgtcggg cgcgggacgc cgcgccaccc gggcgccatc    900
gagacctacc tcttctccat gttcaacgag aaccagaagg agagcggcgt ggagcagaac    960
tgggggctct tctaccccaa catgcagcac gtctacccca tcagcttctg a            1011
```

<210> SEQ ID NO 4
<211> LENGTH: 336
<212> TYPE: PRT
<213> ORGANISM: Zea mays

<400> SEQUENCE: 4

```
Met Ala Ser Arg Gln Gly Val Ala Ala Ser Met Phe Ala Thr Ala Leu
 1               5                  10                  15

Leu Leu Gly Val Phe Ala Ser Ile Pro Gln Ser Ala Glu Ala Ile Gly
            20                  25                  30

Val Cys Tyr Gly Met Ser Ala Asn Asn Leu Pro Ala Ala Ser Thr Val
        35                  40                  45

Val Ser Met Tyr Lys Ala Asn Gly Ile Ser Ala Met Arg Leu Tyr Ala
    50                  55                  60

Pro Asp Gln Gly Ala Leu Gln Ala Val Gly Gly Thr Gly Ile Ser Val
65                  70                  75                  80

Ala Val Gly Ala Pro Asn Asp Val Leu Ser Asn Ile Ala Ala Ser Pro
                85                  90                  95

Ala Ala Ala Ala Ser Trp Val Arg Asn Asn Ile Gln Ala Tyr Pro Ser
            100                 105                 110

Val Ser Phe Arg Tyr Val Cys Val Gly Asn Glu Val Ala Gly Gly Ala
        115                 120                 125

Ala Gln Asp Leu Ala Pro Ala Met Glu Asn Val His Ala Ala Leu Ala
    130                 135                 140

Ala Ala Gly Leu Gly His Ile Lys Val Thr Thr Ser Val Ser Gln Ala
145                 150                 155                 160

Ile Leu Gly Val Tyr Ser Pro Pro Ser Ala Ala Glu Phe Thr Gly Glu
                165                 170                 175

Ala Arg Gly Tyr Met Gly Pro Val Leu Gln Phe Leu Ala Arg Thr Gly
            180                 185                 190

Ser Pro Leu Met Ala Asn Ile Tyr Pro Tyr Leu Ala Trp Ala Tyr Asn
        195                 200                 205

Pro Ser Ala Met Asp Met Ser Tyr Ala Leu Phe Thr Ser Ser Gly Thr
    210                 215                 220

Val Val Gln Asp Gly Ala Tyr Gly Tyr Gln Asn Leu Phe Asp Thr Thr
225                 230                 235                 240

Val Asp Ala Phe Tyr Val Ala Met Gly Asn Asn Gly Gly Ser Gly Val
                245                 250                 255

Pro Leu Val Val Ser Glu Ser Gly Trp Pro Ser Gly Gly Gly Val Gln
            260                 265                 270
```

```
Ala Thr Pro Ala Asn Ala Arg Val Tyr Asn Gln Tyr Leu Ile Asn His
            275                 280                 285

Val Gly Arg Gly Thr Pro Arg His Pro Gly Ala Ile Glu Thr Tyr Leu
            290                 295                 300

Phe Ser Met Phe Asn Glu Asn Gln Lys Glu Ser Gly Val Glu Gln Asn
305                 310                 315                 320

Trp Gly Leu Phe Tyr Pro Asn Met Gln His Val Tyr Pro Ile Ser Phe
                325                 330                 335

<210> SEQ ID NO 5
<211> LENGTH: 951
<212> TYPE: DNA
<213> ORGANISM: Zea mays

<400> SEQUENCE: 5
atgtgcgttt cgatcgcagg tgctgaggcc atcggggtgt gctacggcat gagcgccaac     60
aacctgccgg cggcgagcac ggtggtgagc atgtacaagg cgaacggcat ctcggcgatg    120
cggctgtacg cgccggacca gggcgcgctg caggcggtgg cggcacgggg catcagcgtg    180
gccgtgggcg cccccaacga cgtgctgtcc aacatcgcgg ctagccccgc ggcggccgcg    240
tcgtgggtgc gcaacaacat ccaggcgtac ccgtccgtgt cgttccgcta cgtgtgcgtg    300
ggcaacgagg tggccggcgg cgcggcgcag gacctggcgc cggccatgga gaacgtgcac    360
gcggcgctgg cggcggccgg gctgggccac atcaaggtga cgacgtcggt gtcgcaggcc    420
atcctgggcg tgtacagccc cgtccgtccgcc gcggagttca ccggcgaggc gcgcggatac    480
atgggccccg tgctgcagtt cctggcgcgc accgggtcgc cgctcatggc caacatctac    540
ccgtacctgg cctgggcata caaccccagc gccatggaca tgagctacgc gctcttcacc    600
tcctccggca ccgtcgtgca ggacggcgcc tacgggtacc agaacctctt cgacaccacc    660
gtcgacgcct tctacgtcgc catgggcaac aacggcggct ccggcgtgcc gctcgtggtg    720
tcgaagagcg ggtggccgtc cggcggcggc gtccaggcca cgccggccaa cgcgagggtg    780
tacaaccagt acctcatcaa ccacgtcggg cgcgggacgc cgcgccaccc gggcgccatc    840
gagacctacc tcttctccat gttcaacgag aaccagaagg agagcggcgt ggagcagaac    900
tgggggctct tctaccccaa catgcagcac gtctacccca tcagcttctg a              951

<210> SEQ ID NO 6
<211> LENGTH: 316
<212> TYPE: PRT
<213> ORGANISM: Zea mays

<400> SEQUENCE: 6

Met Cys Val Ser Ile Ala Gly Ala Glu Ala Ile Gly Val Cys Tyr Gly
 1                5                  10                 15

Met Ser Ala Asn Asn Leu Pro Ala Ala Ser Thr Val Val Ser Met Tyr
                20                 25                 30

Lys Ala Asn Gly Ile Ser Ala Met Arg Leu Tyr Ala Pro Asp Gln Gly
             35                  40                 45

Ala Leu Gln Ala Val Gly Gly Thr Gly Ile Ser Val Ala Val Gly Ala
     50                  55                 60

Pro Asn Asp Val Leu Ser Asn Ile Ala Ala Ser Pro Ala Ala Ala Ala
65               70                 75                  80

Ser Trp Val Arg Asn Asn Ile Gln Ala Tyr Pro Ser Val Ser Phe Arg
                 85                 90                 95

Tyr Val Cys Val Gly Asn Glu Val Ala Gly Gly Ala Ala Gln Asp Leu
```

```
                    100                 105                 110
Ala Pro Ala Met Glu Asn Val His Ala Ala Leu Ala Ala Ala Gly Leu
            115                 120                 125

Gly His Ile Lys Val Thr Thr Ser Val Ser Gln Ala Ile Leu Gly Val
        130                 135                 140

Tyr Ser Pro Pro Ser Ala Ala Glu Phe Thr Gly Glu Ala Arg Gly Tyr
145                 150                 155                 160

Met Gly Pro Val Leu Gln Phe Leu Ala Arg Thr Gly Ser Pro Leu Met
                165                 170                 175

Ala Asn Ile Tyr Pro Tyr Leu Ala Trp Ala Tyr Asn Pro Ser Ala Met
            180                 185                 190

Asp Met Ser Tyr Ala Leu Phe Thr Ser Ser Gly Thr Val Val Gln Asp
        195                 200                 205

Gly Ala Tyr Gly Tyr Gln Asn Leu Phe Asp Thr Thr Val Asp Ala Phe
210                 215                 220

Tyr Val Ala Met Gly Asn Asn Gly Gly Ser Gly Val Pro Leu Val Val
225                 230                 235                 240

Ser Lys Ser Gly Trp Pro Ser Gly Gly Val Gln Ala Thr Pro Ala
                245                 250                 255

Asn Ala Arg Val Tyr Asn Gln Tyr Leu Ile Asn His Val Gly Arg Gly
            260                 265                 270

Thr Pro Arg His Pro Gly Ala Ile Glu Thr Tyr Leu Phe Ser Met Phe
        275                 280                 285

Asn Glu Asn Gln Lys Glu Ser Gly Val Glu Gln Asn Trp Gly Leu Phe
    290                 295                 300

Tyr Pro Asn Met Gln His Val Tyr Pro Ile Ser Phe
305                 310                 315

<210> SEQ ID NO 7
<211> LENGTH: 951
<212> TYPE: DNA
<213> ORGANISM: Zea mays

<400> SEQUENCE: 7
atgtgcgttt cgatcgcagg tgctgaggcc atcggggtgt gctacggcat gagcgccaac      60
aacctgccgg cggcgagcac ggtggtgagc atgtacaagg cgaacggcat ctcggcgatg     120
cggctgtacg cgccggacca gggcgcgctg caggcggtgg gcggcacggg catcagcgtg     180
gccgtgggcg cccccaacga cgtgctgtcc aacatcgcgg ctagccccgc ggcggccgcg     240
tcgtgggtgc gcaacaacat ccaggcgtac ccgtccgtgt cgttccgcta cgtgtgcgtg     300
ggcaacgagg tggccggcgg cgcggcgcag gacctggcgc cggccatgga gaacgtgcac     360
gcggcgctgg cggcggccgg gctgggccac atcaaggtga cgacgtcggt gtcgcaggcc     420
atcctgggcg tgtacagccc gccgtccgcc gcggagttca ccggcgaggc gcgcggatac     480
atgggccccg tgctgcagtt cctggcgcgc accggtcgc cgctcatggc caacatctac     540
ccgtacctgg cctgggcata aaccccagc gccatggaca tgagctacgc gctcttcacc     600
tcctccggca ccgtcgtgca ggacggcgcc tacgggtacc agaacctctt cgacaccacc     660
gtcgacgcct tctacgtcgc catgggcaac aacggcggct ccggcgtgcc gctcgtggtg     720
tcggagagcg ggtggccgtc cggcggcggc gtccaggcca gccggccaa cgcgagggtg     780 tacaaccagt acctcatcaa ccacgtcggg cgcgggacgc cgcgccaccc gggcgccatc     840
gagacctacc tcttctccat gttcaacgag aaccagaagg agagcggcgt ggagcagaac     900
tgggggctct tctaccccaa catgcagcac gtctacccca tcagcttctg a              951
```

<210> SEQ ID NO 8
<211> LENGTH: 316
<212> TYPE: PRT
<213> ORGANISM: Zea mays

<400> SEQUENCE: 8

```
Met Cys Val Ser Ile Ala Gly Ala Glu Ala Ile Gly Val Cys Tyr Gly
 1               5                  10                  15

Met Ser Ala Asn Asn Leu Pro Ala Ala Ser Thr Val Val Ser Met Tyr
            20                  25                  30

Lys Ala Asn Gly Ile Ser Ala Met Arg Leu Tyr Ala Pro Asp Gln Gly
         35                  40                  45

Ala Leu Gln Ala Val Gly Gly Thr Gly Ile Ser Val Ala Val Gly Ala
     50                  55                  60

Pro Asn Asp Val Leu Ser Asn Ile Ala Ala Ser Pro Ala Ala Ala
 65                  70                  75                  80

Ser Trp Val Arg Asn Asn Ile Gln Ala Tyr Pro Ser Val Ser Phe Arg
                 85                  90                  95

Tyr Val Cys Val Gly Asn Glu Val Ala Gly Gly Ala Ala Gln Asp Leu
            100                 105                 110

Ala Pro Ala Met Glu Asn Val His Ala Ala Leu Ala Ala Ala Gly Leu
        115                 120                 125

Gly His Ile Lys Val Thr Thr Ser Val Ser Gln Ala Ile Leu Gly Val
    130                 135                 140

Tyr Ser Pro Pro Ser Ala Ala Glu Phe Thr Gly Glu Ala Arg Gly Tyr
145                 150                 155                 160

Met Gly Pro Val Leu Gln Phe Leu Ala Arg Thr Gly Ser Pro Leu Met
                165                 170                 175

Ala Asn Ile Tyr Pro Tyr Leu Ala Trp Ala Tyr Asn Pro Ser Ala Met
            180                 185                 190

Asp Met Ser Tyr Ala Leu Phe Thr Ser Ser Gly Thr Val Val Gln Asp
        195                 200                 205

Gly Ala Tyr Gly Tyr Gln Asn Leu Phe Asp Thr Thr Val Asp Ala Phe
    210                 215                 220

Tyr Val Ala Met Gly Asn Asn Gly Gly Ser Gly Val Pro Leu Val Val
225                 230                 235                 240

Ser Glu Ser Gly Trp Pro Ser Gly Gly Val Gln Ala Thr Pro Ala
                245                 250                 255

Asn Ala Arg Val Tyr Asn Gln Tyr Leu Ile Asn His Val Gly Arg Gly
            260                 265                 270

Thr Pro Arg His Pro Gly Ala Ile Glu Thr Tyr Leu Phe Ser Met Phe
        275                 280                 285

Asn Glu Asn Gln Lys Glu Ser Gly Val Glu Gln Asn Trp Gly Leu Phe
    290                 295                 300

Tyr Pro Asn Met Gln His Val Tyr Pro Ile Ser Phe
305                 310                 315
```

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
acgtgctgtc caacatcg             18

```
<210> SEQ ID NO 10
<211> LENGTH: 21
<212> TYPE: DNA
<213> ORGANISM: Artificial Sequence
<220> FEATURE:
<223> OTHER INFORMATION: Synthetic Construct

<400> SEQUENCE: 10
aggtgatgag tcagccctag c                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Construct

<400> SEQUENCE: 11
accagaacct cttcgacacc a                                              21
```

MAIZE VARIETY AND METHOD OF PRODUCTION

RELATED APPLICATION

This application claims the benefit under 35 USC 119(e) of U.S. Provisional Patent Application No. 61/351,729, filed Jun. 4, 2010, the disclosure of which is hereby incorporated by reference in its entirety.

STATEMENT AS TO RIGHTS TO INVENTIONS MADE UNDER FEDERALLY SPONSORED RESEARCH OR DEVELOPMENT

This invention was made with government support under awarded Contract No. DE-SC0004822, awarded by the United States Department of Energy to The University of California at Berkeley. The government has certain rights in this invention.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 677792000700SEQLIST.txt, date recorded: Jun. 1, 2011, size: 17 kB).

FIELD

The present disclosure is directed to a new variety of maize, Zea mays. In particular, the disclosure relates to a variety of maize containing a candy leaf-1 (Cal-1) allele, whose expression results in increased cell wall-derived glucan content in the maize plant.

BACKGROUND

Members of the grasses represent some of the major economical relevant crops such as wheat, rice and maize. According to the Food and Agriculture Organization, the world production of grasses in 2008 was 2.5 billion metric tons (FAOSTAT: Food and Agriculture Organization of the United Nations, Rome Italy website). In addition to their nutritional importance, grasses have recently attracted attention as potential second generation bioenergy crops due to their potential to produce large quantities of biomass in short times with little agricultural input from growers (Heaton, E A, et al., Global Change Biology 14, 2000-14, 2008).

The grasses are noteworthy for their complex cell wall structure that is distinct from that of dicotyledons such as trees. One profound difference is that heteroxylans constitute the major hemicellulose in their primary cell wall. The cell walls of grasses also have less pectic polysaccharides compared to other higher plants. Another major difference in the primary cell wall is the presence of (1,3;1,4)-β-D-glucans, a polysaccharide that is absent outside the Poales in higher plants. The unique cell wall structure of grasses such as maize has potential to provide large quantities sugars that can be used as feedstocks for the production of biofuels such as ethanol. For example, the glucan-containing components of cell walls of maize can be used in the production of ethanol.

There is a need to develop new varieties of maize that display improved cell wall characteristics such as increased levels of glucose containing polymers.

BRIEF SUMMARY

In order to meet this need, the present disclosure provides an improved maize variety containing a candy leaf-1 Cal-1 allele having one or more mutations in the Cal-1 gene, where the Cal-1 allele encodes a polypeptide with decreased licheninase activity, resulting in a maize plant with elevated levels of glucan, compared to the levels of glucan in a corresponding maize plant lacking the Cal-1 allele.

Accordingly, certain aspects of the present disclosure relates to maize, Zea mays, seed containing a Cal-1 allele, where the seed produces a plant having elevated levels of glucan compared to the levels of glucan in a corresponding maize plant lacking said Cal-1 allele, and where the Cal-1 allele is present in seed having ATCC Accession Number PTA-12213. In one embodiment, the present disclosure is directed to a maize plant and parts isolated therefrom produced by growing the maize seed containing the Cal-1 allele. In another embodiment, the maize plant has at least a 20%, at least a 25%, at least a 30%, at least a 35%, at least a 40%, at least a 50%, at least a 55%, at least a 60%, at least a 65%, at least a 70%, at least a 75%, at least an 80%, at least an 85%, at least a 90%, at least a 95%, at least a 100%, at least a 200%, at least a 300%, at least a 400%, at least a 500%, at least a 600%, at least a 700%, at least an 800%, at least a 900%, at least a 1,000%, or higher percentage increase in the levels of glucan, as compared to the levels of glucan in a corresponding maize plant lacking the Cal-1 allele. In another embodiment, the present disclosure is directed to a plant and parts isolated therefrom having all the physiological and morphological characteristics of a plant produced by growing maize seed having the Cal-1 allele. In still another embodiment, the present disclosure is directed to an $F_1$ hybrid maize seed, plants grown from the seed, and an ear, a cob, a husk, a stalk, a leaf, or a portion thereof isolated therefrom having the maize plant containing the Cal-1 allele as a parent.

In still another embodiment, the present disclosure is directed to a feed product containing at least a portion of a maize plant containing the Cal-1 allele, or plant part therefrom. In certain embodiments, the feed product is an animal feed or human food. In a further embodiment, the present disclosure is directed to silage containing at least a portion of the maize plant containing the Cal-1 allele, or plant part therefrom. In still a further embodiment, the present disclosure is directed to hydrocarbons or hydrocarbon derivatives produced from at least a portion of maize plant containing the Cal-1 allele, or plant part therefrom maize plant containing the Cal-1 allele, or plant part therefrom. In another embodiment, the present disclosure is directed to carbohydrates produced from at least a portion of the maize plant containing the Cal-1 allele, or plant part therefrom.

Maize plant parts include maize ears, cobs, husks, stalks, leaves, parts of leaves, pollen, ovules, flowers, kernels, and the like. In another embodiment, the present disclosure is further directed to maize ears, cobs, husks, or stalks, maize leaves, parts of maize leaves, flowers, kernels, pollen, and ovules isolated from maize plants containing the Cal-1 allele. In another embodiment, the present disclosure is further directed to tissue culture or cells derived from maize plants containing the Cal-1 allele.

In yet another embodiment, the present disclosure is further directed to a method of selecting maize plants by: a) growing maize plants containing the Cal-1 allele, where the maize plants are grown from maize seed containing the Cal-1 allele, and b) selecting a plant from step a). In another embodiment, the present disclosure is further directed to maize plants, plant parts and seeds produced by the maize plants wherein the maize plants are isolated by the selection method of the disclosure. In another embodiment, the present disclosure is further directed to a method of breeding maize plants by crossing a maize plant with a plant grown from the maize seed having the Cal-1 allele. In still another embodiment, the present disclosure is further directed to maize plants, maize parts from the maize plants, and seeds produced therefrom where the maize plant is isolated by the breeding method of the disclosure.

Another aspect of the present disclosure relates to maize seed designated as '236-1' having ATCC Accession Number PTA-12213. In one embodiment, the present disclosure is directed to a maize plant and parts isolated therefrom produced by growing '236-1' maize seed. In another embodiment, the present disclosure is directed to a maize plant and parts isolated therefrom having all the physiological and morphological characteristics of a maize plant produced by growing '236-1' maize seed having ATCC Accession Number PTA-12213. In still another embodiment, the present disclosure is directed to an $F_1$ hybrid maize seed, plants grown from the seed, and an ear, a cob, a husk, or a stalk isolated therefrom having '236-1' as a parent, wherein '236-1' is grown from '236-1' maize seed having ATCC Accession Number PTA-12213.

In still another embodiment, the present disclosure is directed to '236-1' maize plants having cell walls with increased glucan content. In a further embodiment, the present disclosure is directed to a feed product containing at least a portion of a '236-1' maize plant or plant part. In certain embodiments, the feed product may be an animal feed or human food. In a further embodiment, the present disclosure is directed to silage containing at least a portion of a '236-1' maize plant or plant part. In still a further embodiment, the present disclosure is directed to hydrocarbons or hydrocarbon derivatives produced from at least a portion of a '236-1' maize plant or plant part. In another embodiment, the present disclosure is directed to carbohydrates produced from at least a portion of a '236-1' maize plant or plant part.

Maize plant parts include maize ears, cobs, husks, stalks, leaves, parts of leaves, pollen, ovules, flowers, kernels, and the like. In another embodiment, the present disclosure is further directed to maize ears, cobs, husks, or stalks, maize leaves, parts of maize leaves, flowers, kernels, pollen, and ovules isolated from '236-1' maize plants. In another embodiment, the present disclosure is further directed to tissue culture or cells derived from '236-1' maize plants.

In yet another embodiment, the present disclosure is further directed to a method of selecting maize plants by: a) growing '236-1' maize plants wherein the '236-1' plants are grown from maize seed having ATCC Accession Number PTA-12213 and b) selecting a plant from step a). In another embodiment, the present disclosure is further directed to maize plants, plant parts and seeds produced by the maize plants wherein the maize plants are isolated by the selection method of the disclosure. In another embodiment, the present disclosure is further directed to a method of breeding maize plants by crossing a maize plant with a plant grown from '236-1' maize seed having ATCC Accession Number PTA-12213. In still another embodiment, the present disclosure is further directed to maize plants, maize parts from the maize plants, and seeds produced therefrom where the maize plant is isolated by the breeding method of the disclosure.

BRIEF DESCRIPTION OF THE DRAWINGS

The patent or application file contains at least one drawing executed in color. Copies of this patent or patent application publication with color drawings will be provided by the office upon request and payment of the necessary fee.

FIG. 3 (B) shows eleven week old wildtype ('Mo17') and '236-1/Mo17' inbred lines grown in Bucerias, Mexico. Again, no change in growth or morphology was observed.

FIG. 5 (B) diagrammatically depicts the lignin content of '236-1' and wildtype lines (in mass %). No difference is observed.

FIG. 7 depicts the nucleic acid sequence and amino acid sequence of Cal-1 T01 licheninase from the '236-1' maize mutant and wildtype A619 maize. FIG. 7A shows the nucleic acid sequence of Cal-1 T01 from the '236-1' maize mutant (SEQ ID NO: 1); FIG. 7B shows the amino acid sequence of Cal-1 T01 from the '236-1' maize mutant (SEQ ID NO: 2); FIG. 7C shows the nucleic acid sequence of Cal-1 T01 from A619 maize (SEQ ID NO: 3); and FIG. 7D shows the amino acid sequence of Cal-1 T01 from A619 maize (SEQ ID NO: 4). The highlighted regions show the location of the point mutation and corresponding amino acid substitution.

FIG. 8 depicts the nucleic acid sequence and amino acid sequence of Cal-1 T02 licheninase from the '236-1' maize mutant and wildtype A619 maize. FIG. 8A shows the nucleic acid sequence of Cal-1 T02 from the '236-1' maize mutant (SEQ ID NO: 5); FIG. 8B shows the amino acid sequence of Cal-1 T02 from the '236-1' maize mutant (SEQ ID NO: 6); FIG. 8C shows the nucleic acid sequence of Cal-1 T02 from A619 maize (SEQ ID NO: 7); and FIG. 8D shows the amino acid sequence of Cal-1 T02 from A619 maize (SEQ ID NO: 8). The highlighted regions show the location of the point mutation and corresponding amino acid substitution.

BRIEF DESCRIPTION OF THE SEQUENCE LISTING

Figure 1:
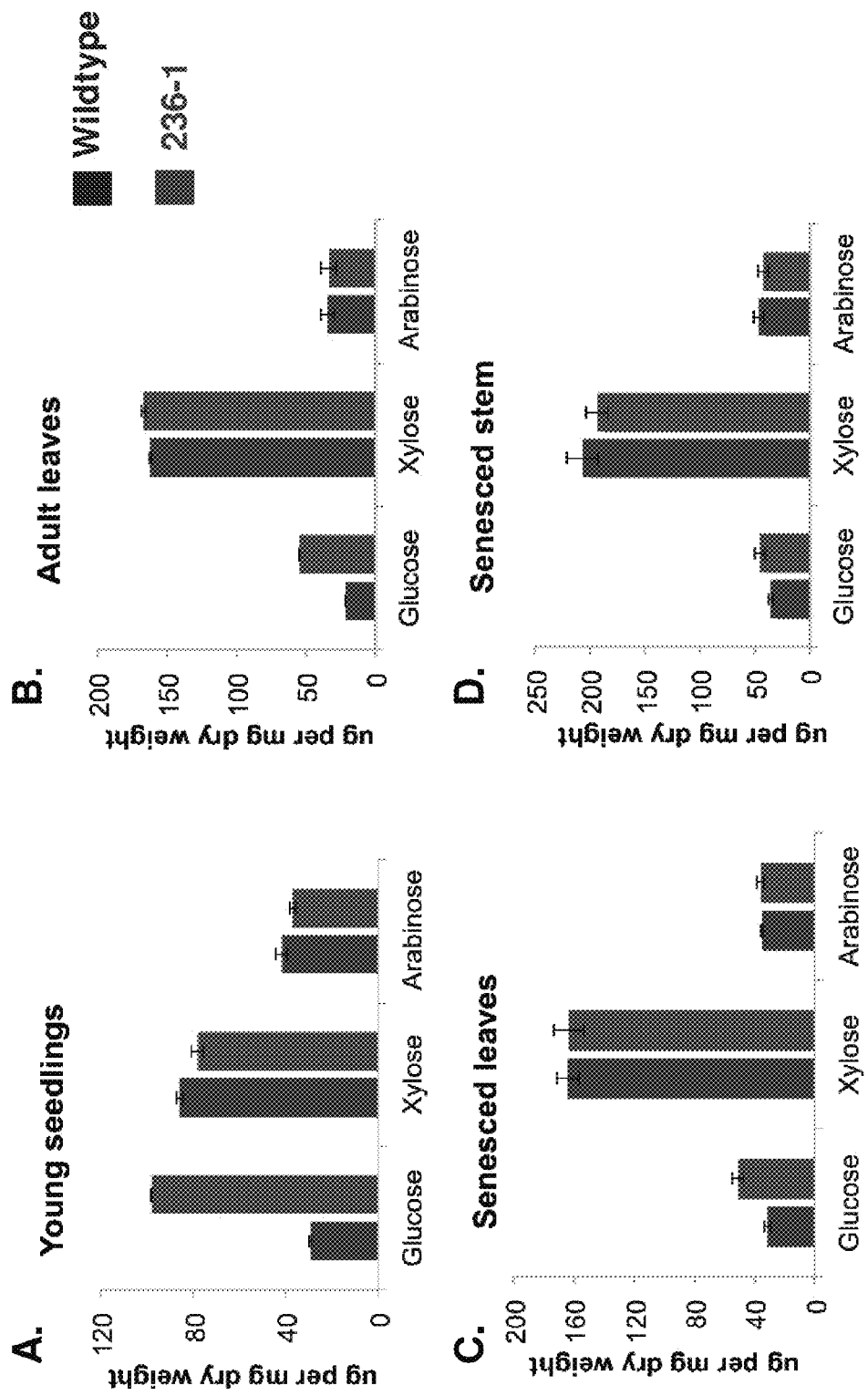
FIG. 1 diagrammatically depicts: (A) the amount of monosaccharides of the hemicellulosic fraction, by weight, produced by young '236-1' maize seedlings; (B) by adult '236-1' maize leaves; (C) by senesced leaf material; and (D) by senesced stem material.

SEQ ID NO: 1 shows the nucleotide coding sequence of the Cal-1 T01 gene from the '236-1' maize mutant.

SEQ ID NO: 2 shows the amino acid sequence encoded by the Cal-1 T01 gene from the '236-1' maize mutant.

SEQ ID NO: 3 shows the nucleotide coding sequence of the Cal-1 T01 gene from wildtype 'A619' maize.

SEQ ID NO: 4 shows the amino acid sequence encoded by the Cal-1 T01 gene from wildtype 'A619' maize.

SEQ ID NO: 5 shows the nucleotide coding sequence of the Cal-1 T02 gene from the '236-1' maize mutant.

SEQ ID NO: 6 shows the amino acid sequence encoded by the Cal-1 T02 gene from the '236-1' maize mutant.

SEQ ID NO: 7 shows the nucleotide coding sequence of the Cal-1 T02 gene from wildtype 'A619' maize.

SEQ ID NO: 8 shows the amino acid sequence encoded by the Cal-1 T02 gene from wildtype 'A619' maize.

SEQ ID NO: 9 shows the nucleic acid sequence of the forward primer used to PCR amplify the GRMZM2G137535 genomic region containing the Cal-1 mutation.

SEQ ID NO: 10 shows the nucleic acid sequence of the reverse primer used to PCR amplify the GRMZM2G137535 genomic region containing the Cal-1 mutation.

SEQ ID NO: 11 shows the nucleic acid sequence of the reverse primer used to sequence the PCR product containing the Cal-1 mutation.

DETAILED DESCRIPTION

The present disclosure relates to maize seed containing a Cal-1 allele encoding a licheninase polypeptide having decreased licheninase activity, resulting in maize with elevated levels of glucan. The present disclosure is based, in part, on a forward genetics approach utilizing a chemically mutagenized maize population that identified mutant maize lines having differing structure, biosynthesis, and metabolism of cell wall polymers. The '236-1' maize line was one such identified mutant which contained a Cal-1 allele. The '236-1' mutant maize containing a Cal-1 allele has a phenotype of elevated levels of glucan, as compared to the levels of glucan in a corresponding maize variety lacking the Cal-1 allele. The elevated levels of glucan in the '236-1' maize provides greater amounts of fermentable glucose, which allows the production of greater amounts of ethanol.

As used herein, "glucan" refers to a polysaccharide of D-glucose monomers linked by glycosidic bonds. Examples of glucans include, without limitation, alpha glucans, such as dextran (α-1,6-glucan with α-1,3-branches) and glycogen (α-1,4- and α-1,6-glucan); and beta glucans, such as lichenin (β-1,3- and (β-1,4-glucan) and cellulose (β-1,4-glucan). In certain embodiments, the present disclosure relates to maize having elevated levels of glucans, such as lichenin. In general, the primary cell walls of grasses, such as maize, contain β-glucans.

Maize Seed Having a Cal-1 Allele

The present disclosure relates, in part to the mutational breeding of maize, and to the selection of maize mutants displaying a phenotype of elevated levels of glucan. As used herein, "mutational breeding" refers to using mutagens, such as chemical mutagens or radiation, to develop variant maize varieties that have an increase in a desired trait (e.g., in this case elevated levels of glucan). Methods of mutational breeding are well known in the art, and examples of suitable methods of mutational breeding are disclosed herein.

Mutations resulting in maize plants having elevated levels of glucans may include, without limitation, one or more mutations in one or more genes involved in the production of glucan, the regulation of glucan, and/or the regulation of genes involved in the production of glucan. For example, one such mutation resulting in plants with elevated levels of glucan may be a mutation in the Cal-1 gene, which encodes a licheninase polypeptide involved in the degradation of the beta glucan lichenin.

One example of a mutant maize plant having elevated levels of glucan that was identified by mutational breeding and selection is the maize variety '236-1'.

The maize variety '236-1' was chosen from mutant maize lines identified from an ethyl methanesulfonate (EMS) mutagenized 'A619' (available from the National Plant Germplasm System, see the USDA Agricultural Research Service website) maize inbred lines after screening for altered wall monosaccharide composition and then crossed with 'Mo17' inbred lines. Briefly, 'A619' maize plants were grown in a field in Missouri, and pollen was collected. The pollen was then sifted to remove any anthers and added to a solution of 0.09% EMS well-dispersed in paraffin oil. The pollen was incubated with the EMS solution for 45 minutes and then was applied to the silks of 'A619' maize plants using a paint brush.

The resulting kernels were sent to Berkeley, Calif. and planted. The plants were selfed, and 20 kernels per ear were grown in trays in a greenhouse. Tissue was then collected from approximately two-week old seedlings for cell wall compositional analysis.

From these seedlings, the '236-1' line was identified as having a higher glucan content in cell wall material and grown to maturity and crossed with the inbred maize line 'Mo17'. The resulting crosses were planted and self-pollinations were made. Kernels from those self-pollinations were grown in the greenhouse again in the spring of 2010, and two-week old seedlings were harvested for analysis. Analysis was conducted on leaf material obtained from the 2nd or 3rd blade tip.

Selection of mutant lines, including the '236-1' line, was based on analyzing alterations in levels of glucan.

The analysis of glucan levels was performed on whole leaf material from 14-day old seedlings, which were freeze-dried after harvest. Analysis of the freeze-dried samples consisted of preparing destarched cell wall material and quantifying the amount of glucan in each mutant maize line. From this evaluation, the '236-1' maize line was selected based on its 286% increase in the levels of glucan compared to levels of glucan in wildtype plants. The '236-1' line was grown and seedlings were harvested. In addition, seedlings were grown to set seeds.

The mutation in the '236-1' maize line was then determined to be a point mutation in the Cal-1 gene. The Cal-1 gene encodes a licheninase polypeptide. As used herein, "licheninase" or "polypeptide with licheninase activity", refers to a polypeptide having E.C. 3.2.1.73 activity, which catalyzes the hydrolysis of 1,4-β-D-glucosidic linkages in β-D-glucans containing 1,3- and 1,4-bonds. A "polypeptide with licheninase activity" includes, without limitation, a licheninase, a lichenase, an endo-β-1,3-1,4 glucanase, a 1,3-1,4-β-D-glucan 4-glucanohydrolase, and a mixed linkage β-glucanase.

Cal-1 Alleles

The present disclosure relates, in part, to the discovery that the '236-1' maize variety contains a Cal-1 allele with a point mutation in the nucleic acid sequence of the Cal-1 gene (SEQ ID NO: 3 and SEQ ID NO: 7). This point mutation encodes a licheninase polypeptide containing a glutamic acid (Glu) to lysine (Lys) amino acid substitution at a catalytic Glu. This altered licheninase polypeptide has decreased licheninase activity, which when expressed in a plant results in an increased cell wall-derived glucan content phenotype. Accordingly, certain aspects of the present disclosure relate to a maize line containing a Cal-1 allele, which when expressed results in the phenotype of elevated levels of glucan.

As used herein an "allele," refers to any of one or more alternative forms of a genetic sequence. In a diploid cell or organism, the two alleles of a given sequence typically occupy corresponding loci on a pair of homologous chromosomes. As used herein, a "Cal-1 allele," refers to an allele of the Cal-1 gene having one or more mutations encoding changes in the corresponding licheninase polypeptide that result in a maize plant having the phenotype of elevated levels of glucan. The changes in the licheninase polypeptide result in a polypeptide having reduced, disrupted, inhibited, or suppressed licheninase activity, which results in the phenotype of elevated levels of glucan.

Accordingly, a Cal-1 allele of the present disclosure contain one or more mutations in the Cal-1 gene that result in a polypeptide with reduced, disrupted, inhibited, or suppressed licheninase activity, which results in the phenotype of elevated levels of glucan. Examples of such mutations include, without limitation, point mutations, nonsense mutations, truncation mutations, missense mutations, substitution mutations, frameshift mutations, loss-of-function mutations, deletion mutations, insertion mutations, duplication mutations, amplification mutations, translocation mutations, or inversion mutations. Methods of identifying genes with one or more mutations are well known in the art, and include nucleic acid sequencing, polymerase chain reaction, or hybridization.

An example of a Cal-1 allele includes, without limitation, the Cal-1 allele present in maize variety '236-1'. The Cal-1 allele of '236-1' contains a point mutation that encodes a Glu to Lys amino acid substitution at either position 262 of the Cal-1 T01 polypeptide sequence (SEQ ID NO: 4) or position 242 of the Cal-1 T02 polypeptide sequence (SEQ ID NO: 8), which results in the phenotype of elevated levels of glucan.

A Cal-1 allele of the present disclosure confers the phenotype of elevated levels of glucan in maize plants containing and expressing the Cal-1 allele. In some embodiments, maize plants containing a Cal-1 allele have at least a 5%, at least a 10%, at least a 15%, at least a 20%, at least a 25%, at least a 30%, at least a 35%, at least a 40%, at least a 50%, at least a 55%, at least a 60%, at least a 65%, at least a 70%, at least a 75%, at least an 80%, at least an 85%, at least a 90%, at least a 95%, at least a 100%, at least a 200%, at least a 300%, at least a 400%, at least a 500%, at least a 600%, at least a 700%, at least an 800%, at least a 900%, at least a 1,000%, or higher percentage increase in the levels of glucan, as compared to the levels of glucan in a corresponding maize plant lacking the Cal-1 allele.

The Cal-1 alleles of the present disclosure may be used in and transferred to different maize varieties and species.

Cal-1 alleles of the present disclosure may be produced by mutagenizing maize and screening for mutant plants displaying the increased cell wall-derived glucan content phenotype and containing a mutation in the Cal-1 gene. Methods of mutagenizing maize are well known in the art. For example, one method of mutagenesis is known as TILLING (for "Targeting Induced Local Lesions in Genomes"). In this method, mutations are induced in the seed of a plant of interest, for example, using a chemical mutagen treatment (Hoffman, *Mutation Research* 75(1): 63-129, 1980), or fast neutron bombardment (Li et al., *Plant Journal* 27(3):235-242, 2001). The resulting plants are grown and self-fertilized, and the progeny are assessed. For example, the plants may be classed using PCR to identify whether a mutated plant has a mutation in a target gene, e.g., that reduces expression of a target gene, or by evaluating whether the plant has increased levels of cell wall-derived glucan content. TILLING can identify mutations that may alter the expression of specific genes or the activity of proteins encoded by these genes (see, Colbert et al. *Plant Physiol* 126:480-484, 2001; McCallum et al. *Nature Biotechnology* 18:455-457, 2000).

Suitable mutagens include, without limitation, ethyl methanesulfonate (EMS), methylmethane sulfonate (MMS), N-ethyl-N-nitrosurea (ENU), trimethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7,12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino]acridine dihydrochloride (ICR-170), and formaldehyde. Additionally, radiation may also be used to mutagenize maize.

The maize plants described herein containing a Cal-1 allele, such as the '236-1' maize variety, and plant parts derived therefrom find numerous uses. For example, they may be used in a breeding program to produce hybrid or inbred maize lines, they may be used in tissue culture, they may be used directly as a feed for animals or as silage, or they may be used to produce hydrocarbons or as a source of carbohydrates.

Maize Breeding

Maize varieties of the present disclosure containing a Cal-1 allele, such as the '236-1' maize variety, may be developed for use in the production of hybrid maize varieties. For example, varieties may be produced to introduce the traits or characteristics of a maize variety containing a Cal-1 allele into other maize lines. However, varieties, such as a maize variety containing a Cal-1 allele, can also provide a source of breeding material that may be used to develop new maize inbred varieties. Plant breeding techniques known in the art and used in a maize plant breeding program include, without limitation, recurrent selection, mass selection, bulk selection, mass selection, backcrossing, pedigree breeding, open pollination breeding, restriction fragment length polymorphism enhanced selection, genetic marker enhanced selection, making double haploids, and transformation. Often combinations of these techniques are used. The development of maize hybrids in a maize plant breeding program requires, in general, the development of homozygous inbred varieties, the crossing of these varieties, and the evaluation of the crosses. There are many analytical methods available to evaluate the result of a cross. The oldest and most traditional method of analysis is the observation of phenotypic traits, but genotypic analysis may also be used.

Accordingly, certain aspects of the present disclosure relate to methods for producing a maize plant by crossing a first parent maize plant with a second parent maize plant, wherein either the first or second parent is a maize variety of the present disclosure containing a Cal-1 allele. The other parent may be any other maize plant, such as another inbred variety or a plant that is part of a synthetic or natural population. Such crossing methods include, without limitation, selfing, sibbing, backcrosses, mass selection, pedigree breeding, bulk selection, hybrid production, crosses to populations, and the like. These methods are well known in the art and some of the more commonly used breeding methods are described below. Descriptions of breeding methods can also be found in, e.g., Allard, *Principles of Plant Breeding*, 1960; Simmonds, *Principles of Crop Improvement*, 1979; and Fehr, "Breeding Methods for Cultivar Development", *Production and Uses*, $2^{nd}$ ed., Wilcox editor, 1987.

Pedigree Breeding

Pedigree breeding starts with the crossing of two genotypes, such as a Cal-1 allele genotype of the present disclosure, and one other elite inbred variety having one or more desirable characteristics that is lacking or which complements a maize variety containing a Cal-1 allele. If the two original parents do not provide all the desired characteristics, other sources can be included in the breeding population. In the pedigree method, superior plants are selfed and selected in successive filial generations. In the succeeding filial generations the heterozygous condition gives way to homogeneous varieties as a result of self-pollination and selection. Typically in the pedigree method of breeding, five or more successive filial generations of selfing and selection is practiced: $F_1 \rightarrow F_2$; $F_2 \rightarrow F_3$; $F_3 \rightarrow F4$; $F_4 \rightarrow F_5$, etc. After a sufficient amount of inbreeding, successive filial generations can serve to increase seed of the developed inbred. Preferably, the inbred variety comprises homozygous alleles at about 95% or more of its loci.

In addition to being used to create a backcross conversion, backcrossing can also be used in combination with pedigree breeding to modify a maize variety containing a Cal-1 allele and a hybrid that is made using the modified maize variety containing a Cal-1 allele. As discussed previously, backcrossing can be used to transfer one or more specifically desirable traits from one variety, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an $F_1$, such as a commercial hybrid, is created. This commercial hybrid may be backcrossed to one of its parent varieties to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Accordingly, some embodiments of the present disclosure relate to a method of obtaining a molecular marker profile of a maize variety containing a Cal-1 allele and using the molecular marker profile to select for a progeny plant with the desired trait (e.g., the phenotype of elevated levels of glucan) and the molecular marker profile of the maize variety containing a Cal-1 allele.

Recurrent Selection and Mass Selection

Recurrent selection may be used with a disclosed maize variety containing a Cal-1 allele to improve a population of plants. The method includes individual plants cross pollinating with each other to form progeny. The progeny are grown and the superior progeny selected by any number of selection methods, which include individual plant, half-sib progeny, full-sib progeny, selfed progeny and toperossing. The selected progeny are cross pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred varieties to be used in hybrids or used as parents for a synthetic cultivar. A synthetic cultivar is the resultant progeny formed by the intercrossing of several selected inbreds.

Additionally, mass selection may be used with a disclosed maize variety containing a Cal-1 allele. Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutational Breeding

Mutation breeding is a method that may be used to introduce new traits into a maize variety of the present disclosure containing a Cal-1 allele. Mutations that occur spontaneously or are artificially induced can be useful sources of variability for a plant breeder. The goal of artificial mutagenesis is to increase the rate of mutation for a desired characteristic. Mutation rates can be increased by many different means including temperature; long-term seed storage; tissue culture conditions; radiation, such as X-rays, Gamma rays (e.g. cobalt 60 or cesium 137), neutrons (products of nuclear fission by uranium 235 in an atomic reactor), Beta radiation (emitted from radioisotopes such as phosphorus 32 or carbon 14), or ultraviolet radiation (preferably from 2500 to 2900 nm); or chemical mutagens, such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in Principles of Cultivar Development Fehr, 1993 Macmillan Publishing Company. In addition, mutations created in other varieties may be used to produce a backcross conversion of a disclosed maize variety containing a Cal-1 allele that comprises such mutations.

Breeding with Molecular Markers

Molecular markers, which include markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs), may be used in plant breeding methods utilizing a disclosed maize variety containing a Cal-1 allele.

Isozyme Electrophoresis and RFLPs have been widely used to determine genetic composition (Lee, M., "Inbred Lines of Maize and Their Molecular Markers," *The Maize Handbook*, Springer-Verlag, New York, Inc. 1994). Isozyme Electrophoresis has a relatively low number of available markers and a low number of allelic variants among maize inbreds. RFLPs allow more discrimination because they have a higher degree of allelic variation in maize and a larger number of markers can be found. Additionally, SSR technology may be used (Smith et al., *Theoretical and Applied Genetics*. Vol. 95:163-173, 1997, and Pejic et al., *Theoretical and Applied Genetics*. Vol. 97:1248-1255, 1998). SSR technology is more efficient and practical to use than RFLPs; more marker loci can be routinely used and more alleles per marker locus can be found using SSRs in comparison to RFLPs. Single Nucleotide Polymorphisms may also be used to identify the unique genetic composition of the disclosure and progeny varieties retaining that unique genetic composition. Various molecular marker techniques may be used in combination to enhance overall resolution.

Maize DNA molecular marker linkage maps have been rapidly constructed and widely implemented in genetic studies (Boppenmaier, et al., *Maize Genetics Cooperative Newsletter.* 65:1991, pg. 90). One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used to reduce the number of crosses back to the recurrent parent needed in a backcrossing program. With backcrossing, the expected contribution of a disclosed maize variety containing a Cal-1 allele after 2, 3, 4 and 5 doses (or 1, 2, 3 and 4 backcrosses) would be 75%, 87.5%, 93.75% and 96.875% respectively. Actual genetic contribution may be much higher than the genetic contribution expected by pedigree, especially if molecular markers are used in selection. The use of molecular markers in the selection process is often called genetic marker enhanced selection. Molecular markers may also be used to confirm and/or determine the pedigree of the progeny variety.

Production of Double Haploids

The production of double haploids may also be used for the development of inbreds in a breeding program. For example, an $F_1$ hybrid for which a disclosed maize variety containing a Cal-1 allele is a parent may be used to produce double haploid plants. Double haploids are produced by the doubling of a set of chromosomes (1N) from a heterozygous plant to produce a completely homozygous individual (Wan et al., *Theoretical and Applied Genetics,* 77:889-892, 1989 and US 2003/0005479. This can be advantageous, as the process omits the generations of selfing needed to obtain a homozygous plant from a heterozygous source.

Haploid induction systems have been developed for various plants to produce haploid tissues, plants and seeds. The haploid induction system can produce haploid plants from any genotype by crossing a selected variety (as female) with an inducer variety. Such inducer varieties for maize include Stock 6 (Coe, 1959, *Am. Nat.* 93:381-382; Sharkar and Coe, 1966, *Genetics* 54:453-464) RWS (Uni-hohenheim web site), KEMS (Deimling, Roeber, and Geiger, 1997, *Vortr. Pflanzenzuchtg* 38:203-224), or KMS and ZMS (Chalyk, et al., 1994, *MNL* 68:47, and Chalyk and Chebotar, 2000, *Plant Breeding* 119:363-364), and indeterminate gametophyte (ig) mutation (Kermicle 1969 Science 166:1422-1424).

Further examples of methods for obtaining haploid plants may be found in, e.g., Kobayashi, M. et al., *Journ. of Heredity* 71(1):9-14, 1980; Pollacsek, M., *Agronomie* (Paris) 12(3): 247-251, 1992; Cho-Un-Haing et al., *Journ. of Plant Biol.,* 1996, 39(3):185-188; Verdoodt, L., et al., February 1998, 96(2):294-300; Genetic Manipulation in Plant Breeding, Proceedings International Symposium Organized by EUCARPIA, Sep. 8-13, 1985, Berlin, Germany; Chalyk et al., 1994, *Maize Genet Coop. Newsletter* 68:47; Chalyk, S. T., 1999, *Maize Genet. Coop. Newsletter* 73:53-54; Coe, R. H., 1959, *Am. Nat.* 93:381-382; Deimling, S. et al., 1997, *Vortr. Pflanzenzuchtg* 38:203-204; Kato, A., 1999, *J. Hered.* 90:276-280; Lashermes, P. et al., 1988, *Theor. Appl. Genet.* 76:570-572 and 76:405-410; Tyrnov, V. S. et al., 1984, *Dokl. Akad. Nauk. SSSR* 276:735-738; Zabirova, E. R. et al., 1996, *Kukuruza I Sorgo* N4, 17-19; Aman, M. A., 1978, *Indian J. Genet Plant Breed* 38:452-457; Chalyk S. T., 1994, *Euphytica* 79:13-18; Chase, S. S., 1952, *Agron. J.* 44:263-267; Coe, E. H., 1959, *Am. Nat.* 93:381-382; Coe, E. H., and Sarkar, K. R., 1964 *J. Hered.* 55:231-233; Greenblatt, I. M. and Bock, M., 1967, *J. Hered.* 58:9-13; Kato, A., 1990, *Maize Genet. Coop. Newsletter* 65:109-110; Kato, A., 1997, *Sex. Plant Reprod.* 10:96-100; Nanda, D. K. and Chase, S. S., 1966, *Crop Sci.* 6:213-215; Sarkar, K. R. and Coe, E. H., 1966, *Genetics* 54:453-464; Sarkar, K. R. and Coe, E. H., 1971, *Crop Sci.* 11:543-544; Sarkar, K. R. and Sachan J. K. S., 1972, *Indian J. Agric. Sci.* 42:781-786; Kermicle J. L., 1969, Mehta Yeshwant, M. R., *Genetics and Molecular Biology,* September 2000, 23(3): 617-622; Tahir, M. S. et al. *Pakistan Journal of Scientific and Industrial Research,* August 2000, 43(4):258-261; Knox, R. E. et al. *Plant Breeding,* August 2000, 119(4):289-298; and U.S. Pat. No. 5,639,951.

Accordingly, certain embodiments of the present disclosure relate to a process for making a homozygous progeny plant of a disclosed maize variety containing a Cal-1 allele that is substantially similar to the maize variety containing a Cal-1 allele by producing or obtaining a seed from the cross of a maize variety containing a Cal-1 allele and another maize plant and applying double haploid methods to the $F_1$ seed or $F_1$ plant or to any successive filial generation. Such methods decrease the number of generations required to produce an inbred with similar genetics or characteristics to the maize variety containing a Cal-1 allele.

Male Sterility and Hybrid Seed Production

Other aspects of the present disclosure relate to the use of any of the disclosure maize varieties containing a Cal-1 allele to produce hybrid seeds. Hybrid seed production requires elimination or inactivation of pollen produced by a female inbred parent. Incomplete removal or inactivation of the pollen provides the potential for self-pollination. A reliable method of controlling male fertility in plants offers the opportunity for improved seed production.

Maize varieties of the present disclosure containing a Cal-1 allele can be produced in a male-sterile form. There are several ways in which a maize plant can be manipulated so that it is male sterile. These include use of manual or mechanical emasculation (or detasseling), use of one or more genetic factors that confer male sterility, including cytoplasmic genetic and/or nuclear genetic male sterility, use of gametocides and the like. A male sterile designated maize plant containing a Cal-1 allele may include one or more genetic factors, which result in cytoplasmic genetic and/or nuclear genetic male sterility. The male sterility may be either partial or complete male sterility.

Hybrid maize seed is often produced by a male sterility system incorporating manual or mechanical detasseling. Alternate strips of two maize inbreds are planted in a field, and the pollen-bearing tassels are removed from one of the inbreds (female). Provided that there is sufficient isolation from sources of foreign maize pollen, the ears of the detasseled inbred will be fertilized only from the other inbred (male), and the resulting seed is therefore hybrid and will form hybrid plants.

The laborious detasseling process can be avoided by using cytoplasmic male-sterile (CMS) inbreds. Plants of a CMS inbred are male sterile as a result of genetic factors in the cytoplasm, as opposed to the nucleus, and so nuclear linked genes are not transferred during backcrossing. Thus, this characteristic is inherited exclusively through the female parent in maize plants, since only the female provides cytoplasm to the fertilized seed. CMS plants are fertilized with pollen from another inbred that is not male-sterile. Pollen from the second inbred may or may not contribute genes that make the hybrid plants male-fertile, and either option may be preferred depending on the intended use of the hybrid. The same hybrid seed, a portion produced from detasseled fertile maize and a portion produced using the CMS system, can be blended to insure that adequate pollen loads are available for fertilization when the hybrid plants are grown. CMS systems have been successfully used since the 1950's, and the male sterility trait is routinely backcrossed into inbred varieties. See Wych, p. 585-586, 1998.

There are several methods of conferring genetic male sterility known in the art, including, without limitation, multiple mutant genes at separate locations within the genome that confer male sterility, as disclosed in U.S. Pat. Nos. 4,654,465 and 4,727,219 and chromosomal translocations as described in U.S. Pat. Nos. 3,861,709 and 3,710,511. In addition to these methods, U.S. Pat. No. 5,432,068, describes a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing, or turning "on", the promoter, which in turn allows the gene that confers male fertility to be transcribed.

Other methods use a variety of approaches such as delivering into the plant a gene encoding a cytotoxic substance associated with a male tissue specific promoter or an antisense system in which a gene critical to fertility is identified and an antisense to that gene is inserted in the plant (see EP 329,308 and WO 90/08828).

Another system for controlling male sterility makes use of gametocides. Gametocides are not a genetic system, but rather a topical application of chemicals. These chemicals affect cells that are critical to male fertility. The application of these chemicals affects fertility in the plants only for the growing season in which the gametocide is applied (see U.S. Pat. No. 4,936,904). Application of the gametocide, timing of the application and genotype specificity often limit the usefulness of the approach and it is not appropriate in all situations.

Incomplete control over male fertility may result in self-pollinated seed being unintentionally harvested and packaged with hybrid seed. This would typically be only female parent seed, because the male plant is grown in rows that are typically destroyed prior to seed development. Once the seed from the hybrid bag is planted, it is possible to identify and select these self-pollinated plants. These self-pollinated plants will be one of the inbred varieties used to produce the hybrid. Though the possibility of a maize variety of the present disclosure containing a Cal-1 allele being included in a hybrid seed bag exists, the occurrence is very low because much care is taken by seed companies to avoid such inclusions. It is worth noting that hybrid seed is sold to growers for the production of grain or forage and not for breeding or seed production. These self-pollinated plants can be identified and selected by one skilled in the art due to their less vigorous appearance for vegetative and/or reproductive characteristics, including shorter plant height, small ear size, ear and kernel shape, cob color, or other characteristics.

Identification of these self-pollinated varieties can also be accomplished through molecular marker analyses (Smith, J. S. C. and Wych, R. D., *Seed Science and Technology* 14, 1-8, 1995). Through these technologies, the homozygosity of the self pollinated variety can be verified by analyzing allelic composition at various loci along the genome. These methods allow for rapid identification of the disclosed varieties (S arca, V. et al., *Probleme de Genetica Teoritica si Aplicata* Vol. 20 (1) p. 29-42).

Accordingly, certain embodiments of the present disclosure relate to a process for producing seed of a disclosed maize variety containing a Cal-1 allele by planting a collection of seed containing seed of a hybrid, one of whose parents is the maize variety containing a Cal-1 allele, where the collection also contains seed of the inbred, growing plants from the collection of seed, identifying inbred parent plants, selecting the inbred parent plant; and controlling pollination to preserve the homozygosity of the inbred parent plant.

Tissue Culture

Other aspects of the present disclosure also relate to the use of a disclosed maize variety containing a Cal-1 allele in tissue culture. As used herein, "tissue culture" includes plant protoplasts, plant cell tissue culture, cultured microspores, plant calli, plant clumps, and the like. As used herein, "growing the seed" or "grown from the seed" include embryo rescue, isolation of cells from seed for use in tissue culture, as well as traditional growing methods.

Methods of regenerating plants from plant tissue culture, such as callus, glume callus, and maize leaf segment cultures, are well known in the art (e.g., Duncan et al., *Planta* 165:322-332, 1985, Songstad et al., *Plant Cell Reports* 7:262-265, 1988, K. P. Rao, et al., *Maize Genetics Cooperation Newsletter,* 60:64-65, 1986, and B. V. Conger, et al., *Plant Cell Reports,* 6:345-347, 1987). Additionally, tissue culture of maize, including tassel/anther culture, is described in U.S. 2002/0062506A1 and European Patent Application, publication EP0160,390. Maize tissue culture procedures are also described in Green and Rhodes, *Maize for Biological Research* (Plant Molecular Biology Association, Charlottesville, Va. 1982, at 367-372); and Duncan, et al., *Planta* 165: 322-332 (1985). Accordingly, other embodiments of the present disclosure provide cells which upon growth and differentiation produce maize plants having the genotype and/or physiological and morphological characteristics of a disclosed maize variety containing a Cal-1 allele.

It will be understood that in addition to the methods of chemical mutagenesis, selection, generating tissue culture from plant material, crossing, and growing plants described herein, any other methods of chemical mutagenesis, selection, generating tissue culture from plant material, crossing, and growing plants known in the art may be used.

Uses of Maize

Maize plants of the present disclosure may be used as human food, livestock feed, and as raw material in industry. The food uses of maize, in addition to human consumption of maize kernels, include both products of dry- and wet-milling industries. The principal products of maize dry milling are grits, meal and flour. The maize wet-milling industry can provide maize starch, maize syrups, and dextrose for food use. Maize oil is recovered from maize germ, which is a by-product of both dry- and wet-milling industries.

Maize, including both grain and non-grain portions of the plant, is also used extensively as livestock feed, primarily for beef cattle, dairy cattle, hogs, and poultry.

Industrial uses of maize include production of ethanol, maize starch in the wet-milling industry, and maize flour in the dry-milling industry. The industrial applications of maize starch and flour are based on functional properties, such as viscosity, film formation, adhesive properties, and ability to suspend particles. The maize starch and flour have application in the paper and textile industries. Other industrial uses include applications in adhesives, building materials, foundry binders, laundry starches, explosives, oil-well muds, and other mining applications.

Plant parts other than the grain of maize may also be used in industry. For example, stalks and husks can be made into paper and wallboard, and cobs can be used for fuel and to make charcoal.

Additionally, maize varieties of the present disclosure containing a Cal-1 allele, such as the '236-1' maize variety, can be utilized for the production of hydrocarbons or hydrocarbon derivatives. "Hydrocarbons" as used herein are organic compounds consisting entirely of hydrogen and carbon. Hydrocarbons include, without limitation, methane, ethane, ethane, ethyne, propane, propene, propyne, cyclopropane, allene, butane, isobutene, butane, butyne, cyclobutane, methylcyclopropane, butadiene, pentane, isopentane, neopentane, pentene, pentyne, cyclopentane, methylcyclobutane, ethylcyclopropane, pentadiene, isoprene, hexane, hexane, hexyne, cyclohexane, methylcyclopentane, ethylcyclobutane, propylcyclopropane, hexadiene, heptane, heptene, heptyne, cycloheptane, methylcyclohexane, heptadiene, octane, octane, octyne, cyclooctane, octadiene, nonane, nonene, nonyne, cyclononane, nonadiene, decane, decene, decyne, cyclodecane, and decadiene.

"Hydrocarbon derivatives" as used herein are organic compounds of carbon and at least one other element that is not hydrogen. Hydrocarbon derivatives include, without limitation, alcohols (e.g., arabinitol, butanol, ethanol, glycerol, methanol, 1,3-propanediol, sorbitol, and xylitol); organic acids (e.g., acetic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, propionic acid, succinic acid, and xylonic acid); esters; ketones (e.g., acetone); aldehydes (e.g. furfural); amino acids (e.g., aspartic acid, glutamic acid, glycine, lysine, serine, and threonine); and gases (e.g. carbon dioxide and carbon monoxide).

Maize plants of the present disclosure can be subjected to wet or dry milling, fermentation, chemical processing, and distillation to produce hydrocarbons or hydrocarbon derivatives. As disclosed herein, hydrocarbons or hydrocarbon derivatives find numerous uses including use as fuels.

Maize plants of the present disclosure can also be utilized for the production of carbohydrates (i.e., saccharides). Carbohydrates include but are not limited to polysaccharides, oligosaccharides, monosaccharides, glucose, glucan, dextrose, sucrose, and fructose. The '236-1' maize plants can be subjected to wet or dry milling, saccharification, and processing to produce the carboydrates. As disclosed herein, carbohydrates find numerous uses including use as food sweeteners and use in the production of fuels.

It will be understood that in addition to the disclosed methods of using the maize plants of the present disclosure for the production of hydrocarbons or hydrocarbon derivatives, any other methods of using maize plants for the production of hydrocarbons or hydrocarbon derivatives known in the art may be used.

Additionally, the seed of a maize variety of the present disclosure containing a Cal-1 allele, the plant produced from the seed, the hybrid maize plant produced from the crossing of the variety, hybrid seed, and various parts of the hybrid maize plant may be utilized for any of the disclosed uses.

EXAMPLES

The following Examples are merely illustrative and are not meant to limit any aspects of the present disclosure in any way.

Example 1

Characterization of the '236-1' Mutant Maize Line

Destarched Cell Wall Material Preparation

The destarched cell wall material preparation was initiated by grinding approximately 60-70 mg of the freeze-dried maize leaf material (Foster C E, et al., Comprehensive Compositional Analysis of Plant Cell Walls (Lignocellulosic biomass) Part II: Carbohydrates. JoVE, 37, 2010). The freeze-dried maize leaf material was ground with 5.5 mm stainless steel balls in a 2 ml screw cap centrifugation tube using a retschmill for 1 min at 25 Hz. The steel balls were removed before continuing with the cell wall isolation procedure.

After grinding the plant material, 1.5 ml of 70% aqueous ethanol was added, and the mixture was vortexed thoroughly. Then, the mixture was centrifuged at 10,000 rpm for 10 min to pellet the alcohol-insoluble residue.

The supernatant was then either aspirated or decanted, and the pellet was washed with 1.5 ml of a chloroform/methanol (1:1 v/v) solution. The tube was shaken thoroughly to resuspend the pellet. The resuspended pellet was then centrifuged at 10,000 rpm for 10 min and the supernatant was aspirated or decanted. The pellet was then resuspended in 500 µl of acetone. The acetone solvent was then evaporated with a stream of air at 35° C. until dry. If needed, dried samples were stored at room-temperature until further processing.

Following the acetone wash, samples were treated with alpha-amylase to remove starch (Foster C E, et al., Comprehensive Compositional Analysis of Plant Cell Walls (Lignocellulosic biomass) Part II: Carbohydrates. JoVE, 37, 2010). To initiate the starch removal, the pellets were resuspended in 1.5 ml of a 0.1 M sodium acetate buffer at pH 5.0. The centrifugation tubes were then capped and heated for 20 min at 80° C. in a heating block. After heat incubation, the tubes were cooled on ice.

After cooling, the following agents were added to digest the pellets: 35 µl of 0.01% sodium azide ($NaN_3$), 35 µl amylase (50 µg/1 mL $H_2O$; from Bacillus species, SIGMA), and 17 µl pullulanase (18.7 units from Bacillus acidopullulyticus; SIGMA). The tubes were then capped and vortexed thoroughly. The pellet suspensions were then incubated overnight at 37° C. in a shaker. The tubes were oriented horizontally to improve mixing.

After incubation, the pellet suspensions were heated at 100° C. for 10 min in a heating block to terminate digestion. The suspensions were then centrifuged at 10,000 rpm for 10 min, and supernatants containing solubilized starch were discarded.

The remaining pellets were washed three times by adding 1.5 ml water, vortexing, centrifuging, and decanting the water.

After the washes, the pellets were resuspended in 500 µl of acetone. The acetone was evaporated with a stream of air at 35° C. until dry. It was sometimes also necessary to break up the material in the tube with a spatula for better drying.

Dried samples were then stored at room-temperature until further processing.

Cell Wall Polysaccharide Composition

Following preparation of the destarched cell wall material, the cell wall polysaccharide composition of each mutant maize line was determined (Foster C E, et al., Comprehensive Compositional Analysis of Plant Cell Walls (Lignocellulosic biomass) Part II: Carbohydrates. *JoVE,* 37, 2010).

First, 2 mg of cell wall material was weighed into 2 ml centrifugation tubes. Then, 20 µl of an inositol solution (5 mg/ml) was added as an internal standard. Following addition of the inositol solution, the tube walls were rinsed with 250 µl of acetone to collect the cell wall material on the bottom of the tube, and then the acetone was evaporated under very gentle airflow.

Acid hydrolysis of the cell wall polysaccharides was then performed (Foster C E, et al., Comprehensive Compositional Analysis of Plant Cell Walls (Lignocellulosic biomass) Part II: Carbohydrates. *JoVE,* 37, 2010). For the acid hydrolysis, 250 µl of 2 M trifluoroacetic acid (TFA) was added to each sample. The TFA was added carefully to ensure that no material was splashed up onto the tube walls.

The tubes containing the samples with the TFA were capped and incubated for 90 min at 121° C. in a heating block. After incubation, the heating blocks containing the sample tubes were cooled on ice. Then, the tubes were centrifuged at 10,000 rpm for 10 min.

After centrifugation, 100 µl of acidic supernatant containing the cell wall polysaccharide-derived monosaccharide from each tube was transferred to a glass screw cap vial, making sure that the pellet material was not disturbed. The TFA in the glass tube was then evaporated under a gentle stream of air in an evaporation device.

Then, 300 µl of 2-propanol was added to each sample, vortexed, and evaporated at 25° C. This procedure was repeated a total of three times.

Following acid hydrolysis, the released monosaccharides were derivatized into their alditol acetates (Foster C E, et al., Comprehensive Compositional Analysis of Plant Cell Walls (Lignocellulosic biomass) Part II: Carbohydrates. *JoVE,* 37, 2010). First, the monosaccharides were reduced to their corresponding alditols. To accomplish this, 200 µl of a freshly prepared sodium borohydride solution was added to each dried sample. The samples were then incubated in the glass vials at room temperature for 1.5 hours. After the incubation, the solution was neutralized by adding 150 µl of glacial acetic acid, vortexing the tubes, and evaporating the glacial acetic acid at 25° C.

Then, 250 µl of an acetic acid/methanol (1:9, v/v) mixture was added to each sample, vortexed, and evaporated at 25° C. and followed by adding 250 µl of methanol and evaporating it under a stream of air. The methanol wash was repeated a total of three times.

Next, the alditols in each sample were acetylated (Foster C E, et al., Comprehensive Compositional Analysis of Plant Cell Walls (Lignocellulosic biomass) Part II: Carbohydrates. *JoVE,* 37, 2010). The acetylation was performed by adding 50 µl of acetic anhydride and 50 µl of pyridine. Then the samples were vortexed and incubating for 20 min at 121° C. in a heating block. The samples were then cooled in the block with ice until the temperature decreased to approximately room temperature. The reagents were then evaporated under a gentle stream of air at room temperature. The samples were then washed three times with toluene by adding 200 µl of toluene and evaporating under air.

The final part of the procedure was to extract the alditol acetates (Foster C E, et al., Comprehensive Compositional Analysis of Plant Cell Walls (Lignocellulosic biomass) Part II: Carbohydrates. *JoVE,* 37, 2010). To accomplish the extraction, 500 µl of ethyl acetate were first added to each sample, and the tubes were swirled lightly. Then, 2 ml of water were added. The tubes were then capped and vortexed. This was followed by centrifuging the tubes at 2,000 rpm for 5 min to obtain clear separate layers, which included ethyl acetate on top and water on bottom.

After centrifugation, 50 µl of the ethyl acetate layer were pipetted into GC/MS (gas chromatography/mass spectrometry) vials with inserts (Foster C E, et al., Comprehensive Compositional Analysis of Plant Cell Walls (Lignocellulosic biomass) Part II: Carbohydrates. *JoVE,* 37, 2010). The samples were then diluted by adding 100 µl of acetone to the GC/MS vials. The vials were then capped and stored at 4° C. when the GC/MS analysis was not immediately performed.

Gas Chromatography/Mass Spectrometry Analysis

For gas chromatography analysis, the samples were injected into a gas chromatograph (GC) that was equipped with a quadrupole mass spectrometer (MS). A Supelco SP-2380 (30 mm×0.25 mm×0.25 µm film thickness) column was used with a 4 min solvent delay and a flow rate of 1.5 ml/min (Foster C E, et al., Comprehensive Compositional Analysis of Plant Cell Walls (Lignocellulosic biomass) Part II: Carbohydrates. *JoVE,* 37, 2010).

The injected samples were subjected to the following temperature program: initial hold at 160° C. for 2 min; a 20° C./min ramp to 200° C. and hold for 5 min; a 20° C./min ramp to 245° C. and hold 12 min; spike to 270° C. and hold for 5 min before cooling to the initial temperature of 160° C. (Foster C E, et al., Comprehensive Compositional Analysis of Plant Cell Walls (Lignocellulosic biomass) Part II: Carbohydrates. *JoVE,* 37, 2010).

Peaks were then identified by mass profiles and/or retention times of standards. Monosaccharides were quantified based on standard curves (Foster C E, et al., Comprehensive Compositional Analysis of Plant Cell Walls (Lignocellulosic biomass) Part II: Carbohydrates. *JoVE,* 37, 2010).

Evaluation of Mutant Maize Lines

From the GC/MS analysis 12 different EMS mutant maize lines were identified with a different abundance of various cell wall polysaccharides compared to 'Mo17'. The abundance of the polysaccharides was determined by measuring the monosaccharide subunits of the cell wall polysaccharides. Table 1 below shows the abundance of arabinose, xylose, and glucose derived from polysaccharides, in the cell walls of each of the 12 mutant lines compared to the corresponding tissue of 'Mo17'. The evaluation showed that some of the mutant maize lines (Mutants 12-1, 12-2, and 12-3) had a higher abundance of polysaccharide-derive arabinose and xylose compared to 'Mo17'. The evaluation also showed that the mutant maize line '236-1' had a much higher abundance of glucan-derived glucose compared to 'Mo17' (Table 1).

TABLE 1

| Sample | Arabinose | Xylose | Glucose |
| --- | --- | --- | --- |
| Mutant 1 | −30% | −29% | |
| Mutant 2 | −38% | −32% | |
| Mutant 3 | | | +70% |
| Mutant 4 | +32% | +28% | |
| Mutant 5 | +46% | +45% | |
| Mutant 6 | +21% | +21% | −49% |
| Mutant 7 | +54% | +29% | |
| Mutant 8 | −15% | −10% | |
| Mutant 9 | +26% | +28% | +71% |
| Mutant 10 | +11% | +11% | +22% |
| '236-1' | | | +286% |
| Mutant 12 | +35% | +18% | |

From this evaluation, the '236-1' maize line was selected based on its 286% increase in levels of cell wall-derived glucose, corresponding to elevated levels of glucan. The '236-1' line was grown and some seedlings were harvested. In addition, some seedlings were grown to set seeds.

Example 2

Figure 2:
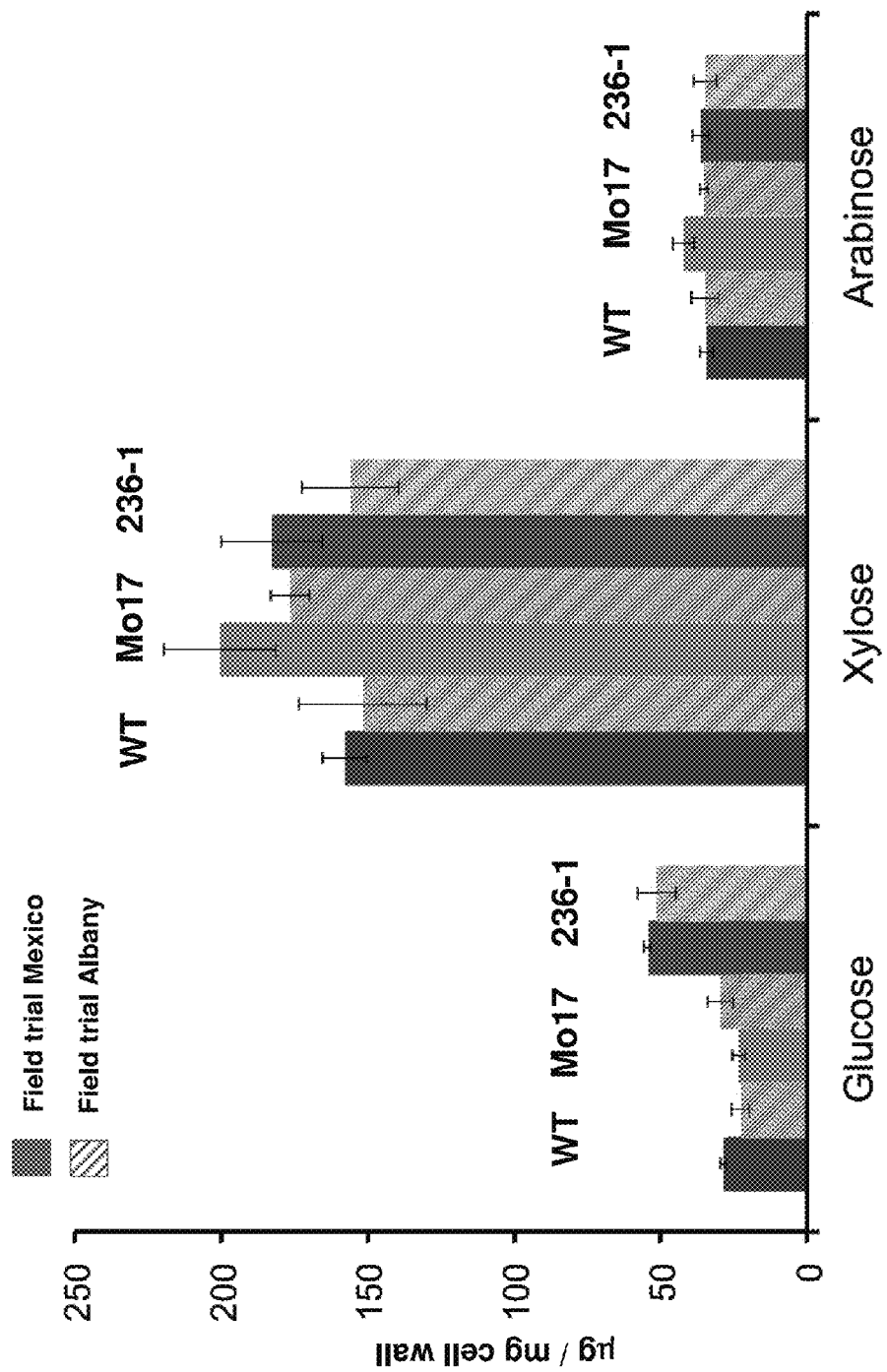
FIG. 2 diagrammatically depicts the amount of monosaccharides of the hemicellulosic fraction, by weight, produced by adult '236-1' leaves in field trials conducted in Albany, Calif. USA and Bucerias, Nayarit, Mexico. The material was harvested 10-11 weeks after planting.

Characterization of Polysaccharide Composition of the '236-1' Mutant Maize Line The '236-1' maize line was further characterized by comparing the hemicellulosic levels of glucan to wildtype maize ('Mo17'). The levels of glucan were determined by measuring the amount of glucose released by the glucan. Analysis was performed on two-week old (young seedling) and eleven-week old leaf material (adult leaves), as well as senesced leaf and stem material (FIG. 1). In all tissues, '236-1' showed an increase of glucose released by weak acid hydrolysis (FIG. 1). Additionally, in field trials conducted in California and Mexico, adult leaf material of '236-1' also showed an increase of glucose released by weak acid hydrolysis using the same method (FIG. 2).

Figure 3:
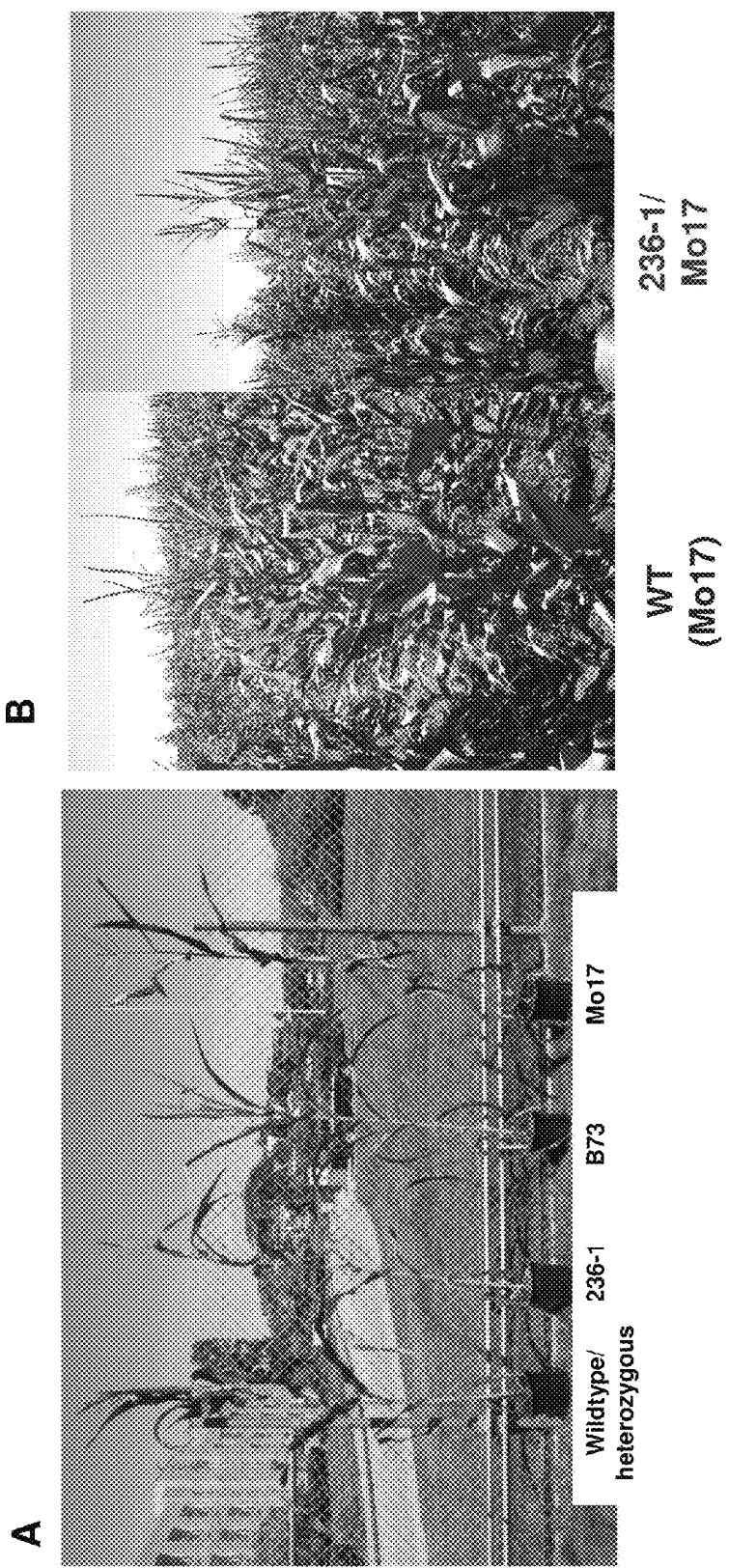
FIG. 3 (A) shows eleven-week old wildtype/heterozygous, '236-1', 'B73', and 'Mo17' maize plants. '236-1' is a maize variety which resulted from a cross between a chemically mutagenized 'A619' line to the 'Mo17' inbred line. The mutant does not display any changes in growth or morphology.

The growth and morphology of the '236-1' maize line was also evaluated. Eleven-week old '236-1' maize plants were compared with 11-week old wildtype/heterozygous maize plants, 1373' maize plants, and 'Mo17' maize plants grown in a greenhouse (FIG. 3A), and in the field in Mexico (FIG. 3B). The '236-1' maize line, which has an 'A619' background crossed to 'Mo17', is depicted here. The comparison showed that the '236-1' maize line does not display any changes in growth or morphology (FIG. 3).

The origin of the elevated levels of glucan was also assessed. An extraction of wall material from mature leaves indicated that the elevated levels of glucan, as measured by the amount of released glucose, was found in a 4M potassium hydroxide fraction (FIG. 4A). This indicated that the glucan is of hemicellulosic nature rather than cellulosic. Glycosidic linkage analysis of that fraction indicated that the increased glucan content includes a mixed-linked β-1,3-1,4-glucan (i.e., lichenin), which is a grass-specific, transient hemicellulosic polymer (FIG. 4B).

The residue remaining residue after 4M potassium hydroxide extraction of the leaf material was mainly composed of crystalline cellulose. This was confirmed by monosaccharide composition analysis, which showed that glucose was the predominant component (FIG. 5A). Additionally, levels of cellulose in adult leaf material from '236-1' were compared with levels in adult leaf material of wildtype. This comparison showed no statistically significant difference (FIG. 5A).

The amount of acetylbromide-soluble lignin was also determined for the '236-1' maize line (Foster C E, et al., Comprehensive Compositional Analysis of Plant Cell Walls (Lignocellulosic biomass) Part I: Lignin. JoVE, 37, 2010). Levels of acetylbromide soluble lignin in adult leaf material from '236-1' were compared with levels in adult leaf material of wildtype. This comparison showed no statistically significant difference in acetylbromide soluble lignin content (FIG. 5B).

Figure 6:
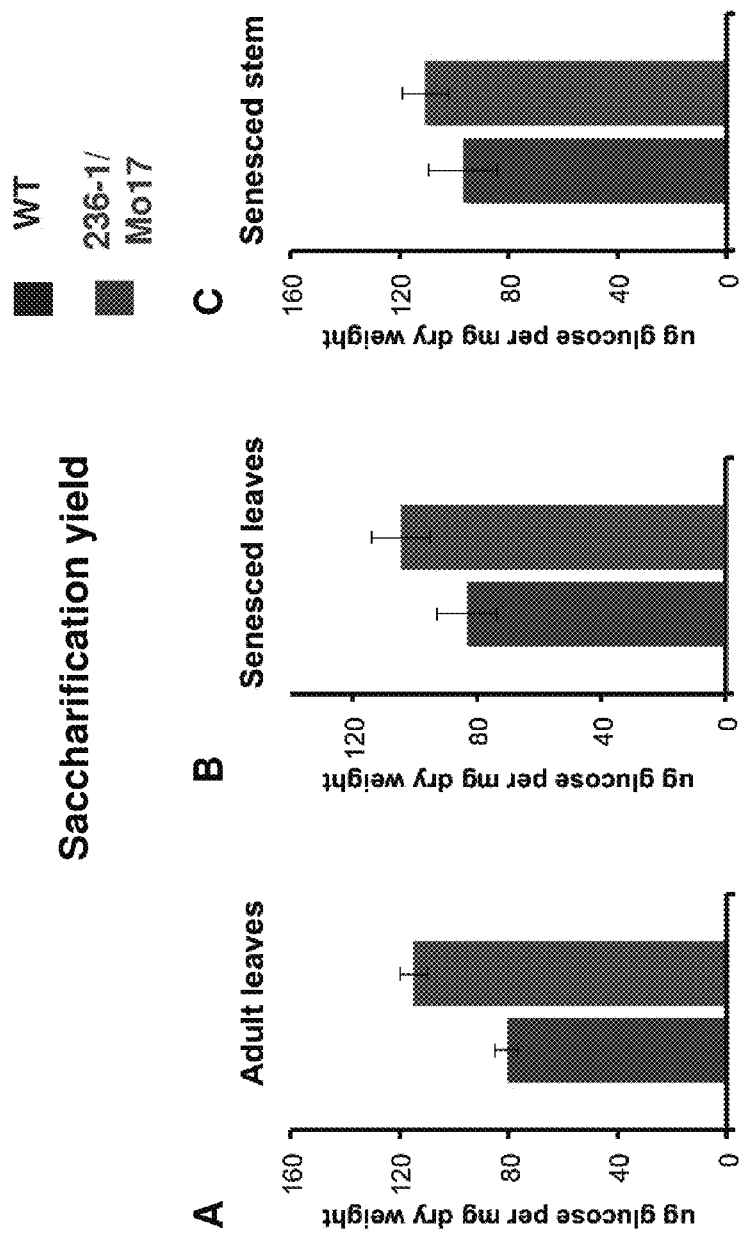
FIG. 6A diagrammatically depicts: (A) the amount of glucose, by weight, produced by '236-1' maize leaf material during saccharification of wall material with a mixture of wall degrading enzymes; (B) the saccharification yield (glucose) derived from senesced leaves; and (C) the saccharification yield (glucose) derived from senesced stem.

The '236-1' maize line was then evaluated to determine the amount of glucose released by saccharification of cell wall material. Destarched alcohol-insoluble residue from adult leaf material from wildtype and '236-1' maize lines was subjected to a saccharification assay using a commercial enzyme mix containing multiple enzyme activities, mainly exoglucanase, endoglucanase, hemi-cellulase, and beta-glucosidase. After incubation for 17 hours, the released glucose amount was assayed using a Megazyme GOPOD kit (K-GLUC, Megazyme, Ireland). The '236-1' maize line showed a 40% increase in glucose saccharification yield compared to the wildtype (FIG. 6A). Significant increases in glucose saccharification levels were also observed in senesced leaves (FIG. 6B) and senesced stems (FIG. 6C).

Figure 4:
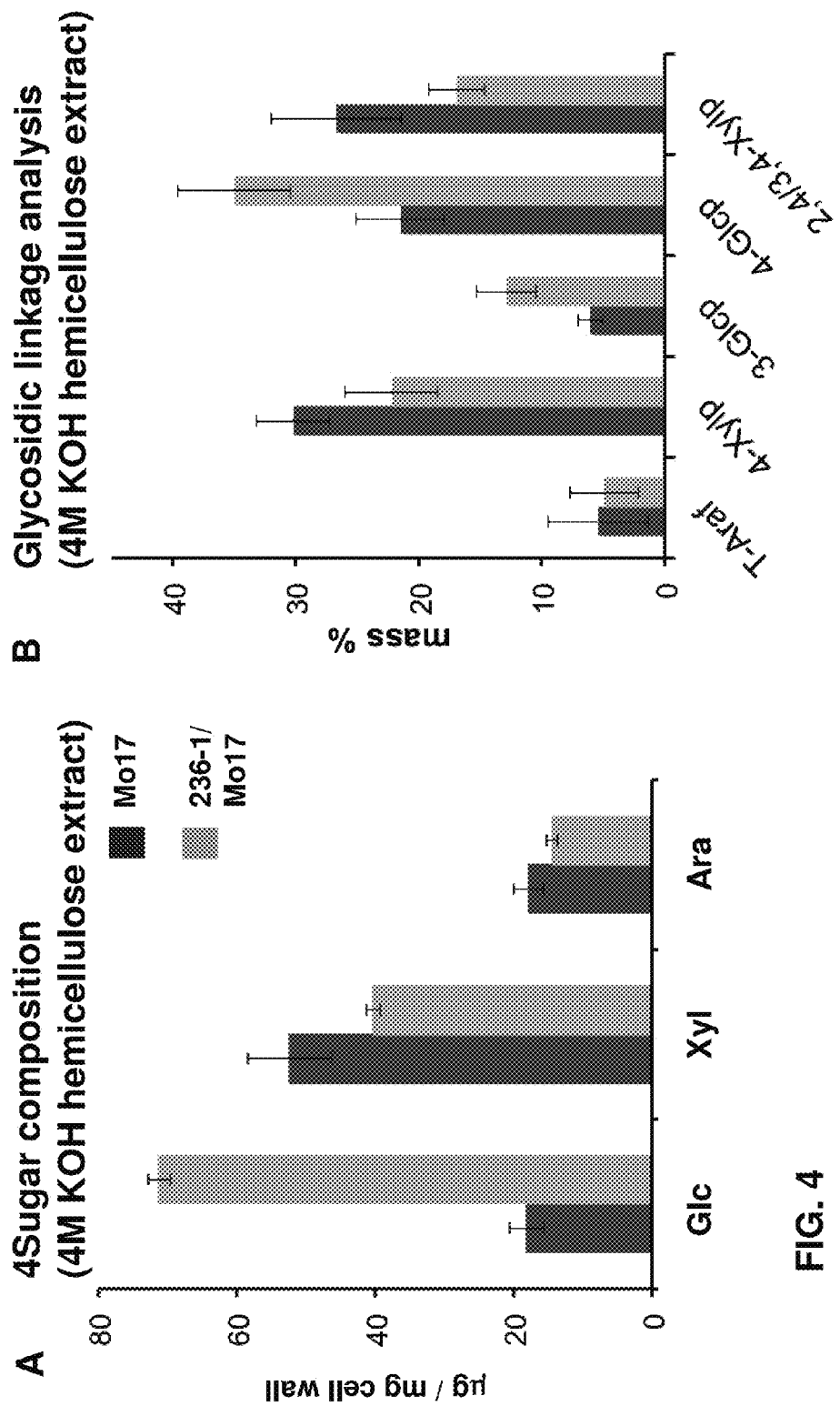
FIG. 4 diagrammatically depicts: (A) the monosaccharide composition, by weight, of a hemicellulose extract (extraction by 4 molar potassium hydroxide) derived maize seedlings from wildtype ('Mo17') and '236-1/Mo17' inbred lines, indicating that the high glucan content is present in the hemicellulosic fraction; and (B) the glycosidic linkage composition, by mol %, of that 4M potassium hydroxide fraction, indicating that the high glucan content is due to an increase in (1,3,1,4)-β-glucan compared to wildtype maize.
Figure 5:
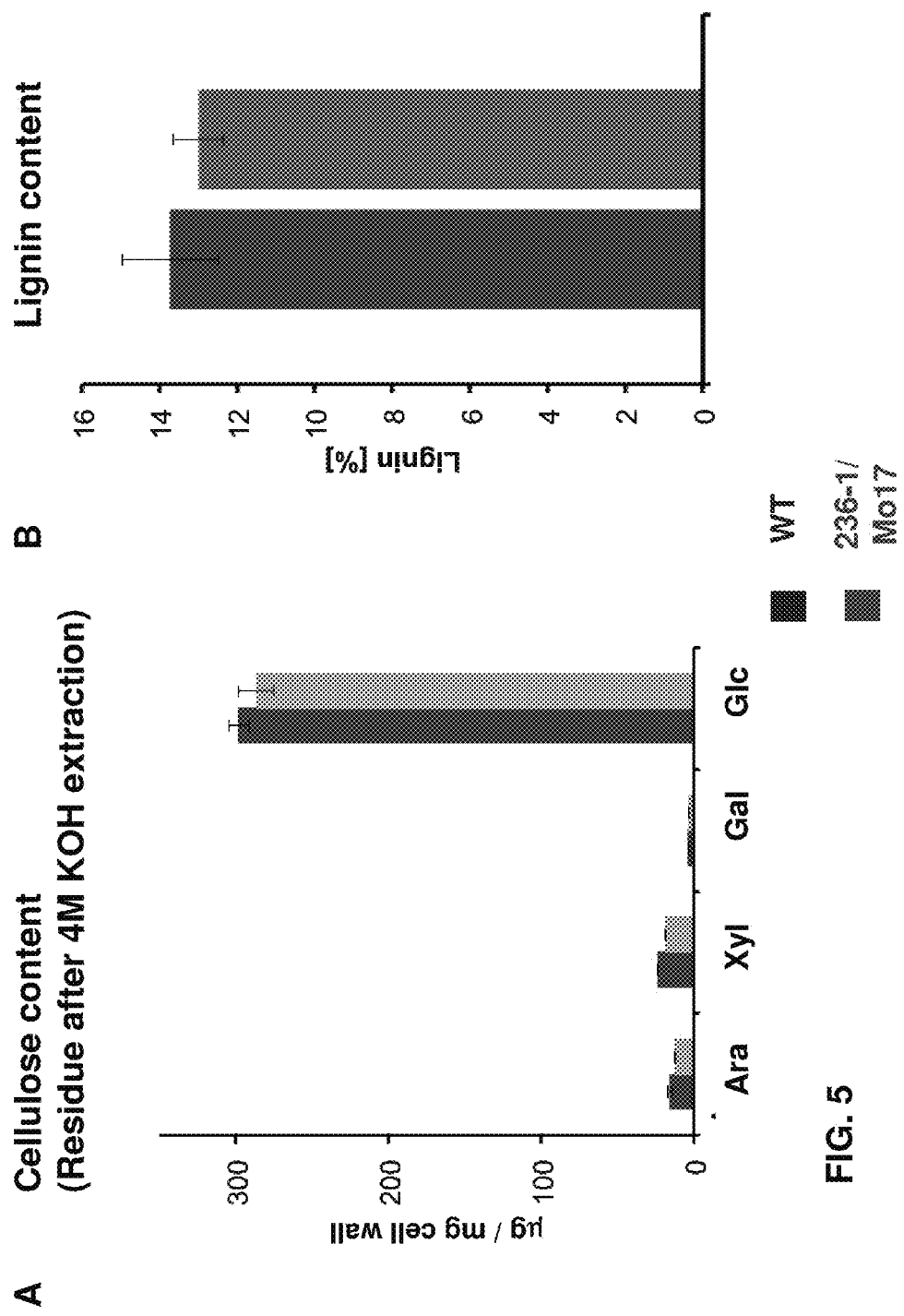
FIG. 5 (A) diagrammatically depicts the monosaccharide composition of the total hydrolysate of the residue after 4M potassium hydroxide extraction. The main component is glucose representing cellulose. Hence, no difference in cellulose-content is observed.

These characterizations show that the '236-1' maize line exhibits an increase in cell wall glucan level compared to wildtype maize. In particular, the '236-1' line showed increased levels of cell wall-derived mixed-linked hemicellulosic glucan (FIGS. 1, 2, and 4). However, the '236-1' line showed no change in crystalline cellulose content or acetyl-bromide-soluble lignin (FIG. 5). Moreover, the '236-1' maize line did not display any growth or morphological phenotype (FIG. 3). Further, when subjected to a saccharification assay, the '236-1' line showed a 40% increase in cell wall released glucose compared to the wildtype line. Thus, the '236-1' maize line has improved characteristics for use as a bioenergy crop.

Example 3

Mapping the '236-1' Maize Mutation

The underlying mutation was mapped to a region of maize chromosome 6 that spans an interval of 140.31 to 144.16 Mbp (GRMZM2G137535). Classical mapping procedures were used to identify this region (Neuffer, M G, Mutation induction in maize. In W F Sheridan, ed, Maize for Biological Research. Plant Mol. Biol. Assoc., Charlottesville, Va., pp 61-64, 1982; and Neuffer, M G, Mutagenesis. In M Freeling, V Walbot, eds, The Maize Handbook. Springer-Verlag, New York, pp 212-219, 1993). Putative proteins encoded in this region were manually annotated by comparison to homologous proteins in rice. Among these putative proteins, Cal-1 gene, encoding a CH17 licheninase, was identified as a gene that harbors the mutation. The GRMZM2G137535 region contains two gene models of the Cal-1 licheninase gene which were named Cal-1 T01 and Cal-1 T02. The gene was then sequenced.

The GRMZM2G137535 region containing the Cal-1 mutation was then amplified and sequenced to identify the Cal-1 mutation. Briefly, the GRMZM2G137535 region containing the Cal-1 mutation was amplified by PCR in multiple segments. The segment carrying the mutation was produced using the forward primer 5'-ACG-TGC-TGT-CCA-ACA-TCG-3' (SEQ ID NO: 9) and the reverse primer 5'-AGG-TGA-TGA-GTC-AGC-CCT-AGC-3' (SEQ ID NO: 10). The PCR was performed using a primer concentration of 40 pmol for each primer in a total volume of 50 µl with Sigma REDTag Ready mix (Sigma-Aldrich). The reaction conditions consisted of an initial 2 min denaturing step at 94° C., followed by 35 cycles of denaturing, annealing and amplification at 94° C. for 30 s, 58° C. for 30 s, and 72° C. for two min respectively. After completion of the last cycle, the reaction was left at 72° C. for an additional 15 min before being cooled to 4° C. The PCR product was then purified using the QIAquick PCR purification kit (Qiagen). The mutation was identified by sequencing the purified PCR product using the primers 5'-ACG-TGC-TGT-CCA-ACA-TCG-3' (SEQ ID NO: 9) and 5'-ACC-AGA-ACC-TCT-TCG-ACA-CCA-3' (SEQ ID NO: 11) in independent sequencing reactions. The results of this analysis are described below.

Figure 7:
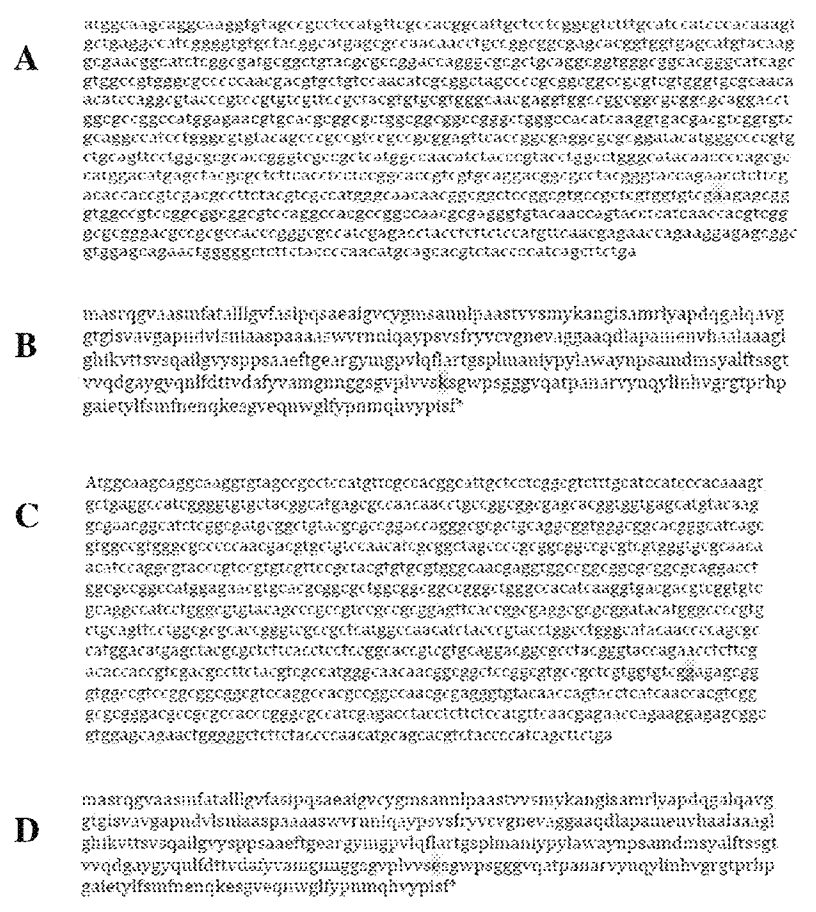

The nucleotide and amino acid sequences of Cal-1 T01 from the '236-1' mutant are shown in FIGS. 71A and 7B, respectively. The nucleotide sequence of Cal-1 T01 from the '236-1' mutant is set forth as SEQ ID NO: 1. The amino acid sequence of Cal-1 T01 from the '236-1' mutant is set forth as SEQ ID NO: 2. The nucleotide and amino acid sequences of Cal-1 T01 from wildtype A619 maize is shown in FIGS. 7C and 7D, respectively. The nucleotide sequence of Cal-1 T01 from wildtype A619 maize is set forth as SEQ ID NO: 3. The amino acid sequence of Cal-1 T01 from wildtype A619 maize is set forth as SEQ ID NO: 4. A comparison of the two sequences shows that the '236-1' mutant contains a "g" to "a" point mutation in the nucleotide sequence of Cal-1 T01, corresponding to a Glu to Lys substitution at position 262 of the amino acid sequence.

Figure 8:
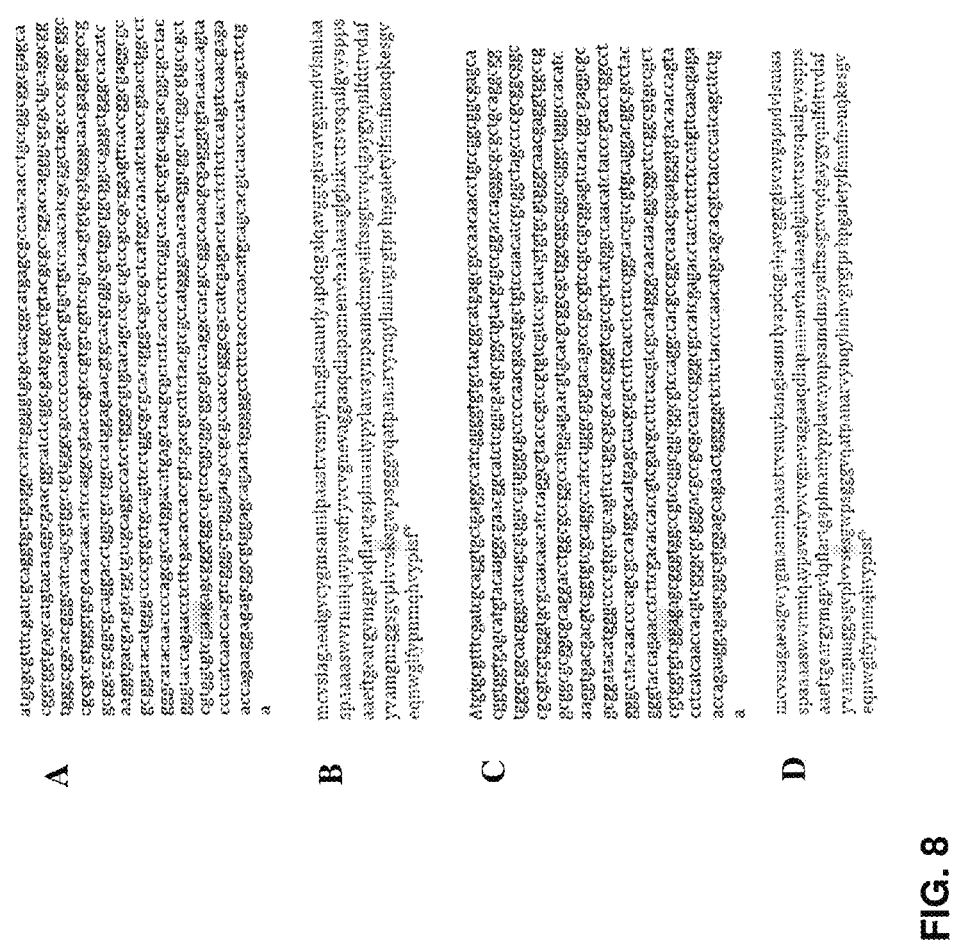

The nucleotide and amino acid sequences of Cal-1 T02 from the '236-1' mutant are shown in FIGS. 8A and 8B, respectively. The nucleotide sequence of Cal-1 T02 from the '236-1' mutant is set forth as SEQ ID NO: 5. The amino acid sequence of Cal-1 T02 from the '236-1' mutant is set forth as SEQ ID NO: 6. The nucleotide and amino acid sequences of Cal-1 T02 from wildtype A619 maize is shown in FIGS. 8C and 8D, respectively. The nucleotide sequence of Cal-1 T02 from wildtype A619 maize is set forth as SEQ ID NO: 7. The amino acid sequence of Cal-1 T01 from wildtype A619 maize is set forth as SEQ ID NO: 8. A comparison of the two sequences shows that the that the '236-1' mutant contains a "g" to "a" point mutation in the nucleotide sequence of Cal-1 T02, corresponding to a Glu to Lys substitution at position 242 of the amino acid sequence.

Deposit Information

Applicants have made available to the public without restriction a deposit of at least 2500 seeds comprising the Cal-1 mutant allele with the American Type Culture Collection (ATCC), University Blvd., Manassas, Va. 20110-2209, USA, with a deposit on Nov. 3, 2011, which has been assigned ATCC number PTA-12213.

The deposit will be maintained in the ATCC depository, which is a public depository, for a period of 30 years, or 5 years after the most recent request, or for the effective life of the patent, whichever is longer, and will be replaced if the deposit becomes nonviable during that period.

The invention claimed is:

1. Maize seed comprising a Cal-1 allele, wherein said seed produces a plant having elevated levels of glucan compared to the levels of glucan in a corresponding maize plant lacking said Cal-1 allele, and wherein the Cal-1 allele is present in seed having ATCC Accession Number PTA-12213.

2. A maize plant produced by growing the seed of claim 1.

3. The maize plant of claim 2, wherein the plant has at least a 20% increase in the levels of glucan, as compared to the levels of glucan in a corresponding maize plant lacking the Cal-1 allele.

4. A plant part from the plant of claim 2.

5. The plant part of claim 4, wherein said part is an ear, a cob, a husk, a stalk, a leaf, or a portion thereof.

6. A feed product comprising the plant of claim 2 or a part thereof.

7. The feed product of claim 6, wherein said feed product is an animal feed or human food.

8. Silage comprising the plant of claim 2 or a part thereof.

9. An $F_1$ hybrid maize plant having a parent that is grown from the seed of claim 1, wherein the $F_1$ hybrid maize plant comprises the Cal-1 allele.

10. An ovule or pollen of the plant of claim 2.

11. A tissue culture of the plant of claim 2.

12. A method of producing maize seeds comprising the steps of crossing the plant of claim 2 with another maize plant and harvesting seed therefrom.

13. Maize seed designated as 236-1 having ATCC Accession Number PTA-12213.

14. A maize plant produced by growing the seed of claim 13.

15. A plant part from the plant of claim 14.

16. The plant part of claim 15, wherein said part is an ear, a cob, a husk, a stalk, a leaf, or a portion thereof.

17. A feed product comprising the plant of claim 14 or a part thereof.

18. Silage comprising the plant of claim 14 or a part thereof.

* * * * *